US011027091B2

(12) United States Patent
 Eisterhold

(10) Patent No.: US 11,027,091 B2
(45) Date of Patent: Jun. 8, 2021

(54) SYSTEMS AND METHODS FOR AN ADAPTIVE AND INTERACTIVE HEALING ENVIRONMENT

(71) Applicant: Gerard Eisterhold, Kansas City, MO (US)

(72) Inventor: Gerard Eisterhold, Kansas City, MO (US)

( * ) Notice: Subject to any disclaimer, the term of this patent is extended or adjusted under 35 U.S.C. 154(b) by 347 days.

(21) Appl. No.: 16/235,578

(22) Filed: Dec. 28, 2018

(65) Prior Publication Data
 US 2019/0134345 A1    May 9, 2019

Related U.S. Application Data

(63) Continuation of application No. 15/174,835, filed on Jun. 6, 2016, now Pat. No. 10,220,182, which is a
(Continued)

(51) Int. Cl.
  *A61M 21/00* (2006.01)
  *G08C 19/16* (2006.01)
  (Continued)

(52) U.S. Cl.
  CPC ............ *A61M 21/00* (2013.01); *G08C 17/02* (2013.01); *G08C 19/00* (2013.01); *G08C 19/16* (2013.01); *G08C 23/04* (2013.01); *A61M 2021/005* (2013.01); *A61M 2021/0027* (2013.01); *A61M 2205/3303* (2013.01); *A61M 2205/3306* (2013.01); *A61M 2205/3375* (2013.01); *A61M 2205/3561* (2013.01); *A61M 2205/58* (2013.01); *A61M 2230/04* (2013.01);
  (Continued)

(58) Field of Classification Search
  CPC .......... A61M 21/00; A61M 2021/0027; A61M 2021/005; A61M 2205/3303; A61M 2205/3306; A61M 2205/3375; A61M 2205/3561; A61M 2205/58; A61M 2230/04; A61M 2230/20; A61M 2230/50; A61M 2230/63; G08C 17/02; G08C 19/00; G08C 23/04; G08C 19/16; G08C 2201/93
  See application file for complete search history.

(56) References Cited

U.S. PATENT DOCUMENTS 5,187,506 A   2/1993  Carter
5,681,259 A  10/1997  August
(Continued)

*Primary Examiner* — Kaylee R Wilson
(74) *Attorney, Agent, or Firm* — Avant Law Group, LLC

(57) ABSTRACT

A method of configuring a personal living environment of a long-term patient comprises providing a central computer controllable via a remote unit. The central computer is coupled to a plurality of output devices, including displays and speakers, and at least one sensor. The method comprises arranging the plurality of output devices in the personal living environment and presenting on at least one display patient selectable objective parameters and subjective parameters. The method comprises obtaining an input from the patient, and in response to the input, representing on the at least one display a relationship, characterized over a time period, between the subjective parameters and the objective parameters selected by the patient. The method comprises shifting presentation of content from one of the plurality of output devices to another of the plurality of output devices based on a proximity of the patient detected by the at least one sensor.

20 Claims, 12 Drawing Sheets

Related U.S. Application Data continuation of application No. 13/748,453, filed on Jan. 23, 2013, now Pat. No. 9,361,791.

(60) Provisional application No. 61/589,749, filed on Jan. 23, 2012.

(51) Int. Cl.
*G08C 17/02* (2006.01)
*G08C 19/00* (2006.01)
*G08C 23/04* (2006.01)

(52) U.S. Cl.
CPC ..... *A61M 2230/20* (2013.01); *A61M 2230/50* (2013.01); *A61M 2230/63* (2013.01); *G08C 2201/93* (2013.01)

(56) References Cited

U.S. PATENT DOCUMENTS

| | | |
|---|---|---|
| 6,182,408 B1 | 2/2001 | Poehler |
| 6,322,502 B1 | 11/2001 | Schoenberg et al. |
| 7,185,866 B2 | 3/2007 | Lee et al. |
| 2004/0010184 A1 | 1/2004 | Kenknight et al. |
| 2004/0172326 A1 | 9/2004 | Yeo et al. |
| 2005/0229200 A1 | 10/2005 | Kirkland et al. |
| 2007/0299694 A1 | 12/2007 | Merck |
| 2008/0106374 A1 | 5/2008 | Sharbaugh |
| 2009/0154737 A1 | 6/2009 | Ostler |
| 2010/0212087 A1 | 8/2010 | Leib et al. |
| 2010/0261979 A1 | 10/2010 | Kiani |
| 2011/0022468 A1 | 1/2011 | Muster |
| 2011/0214153 A1 | 9/2011 | Rosenfeld |
| 2012/0201908 A1 | 8/2012 | Miller |
| 2012/0227337 A1 | 9/2012 | Li |
| 2013/0166193 A1 | 6/2013 | Goldman et al. |

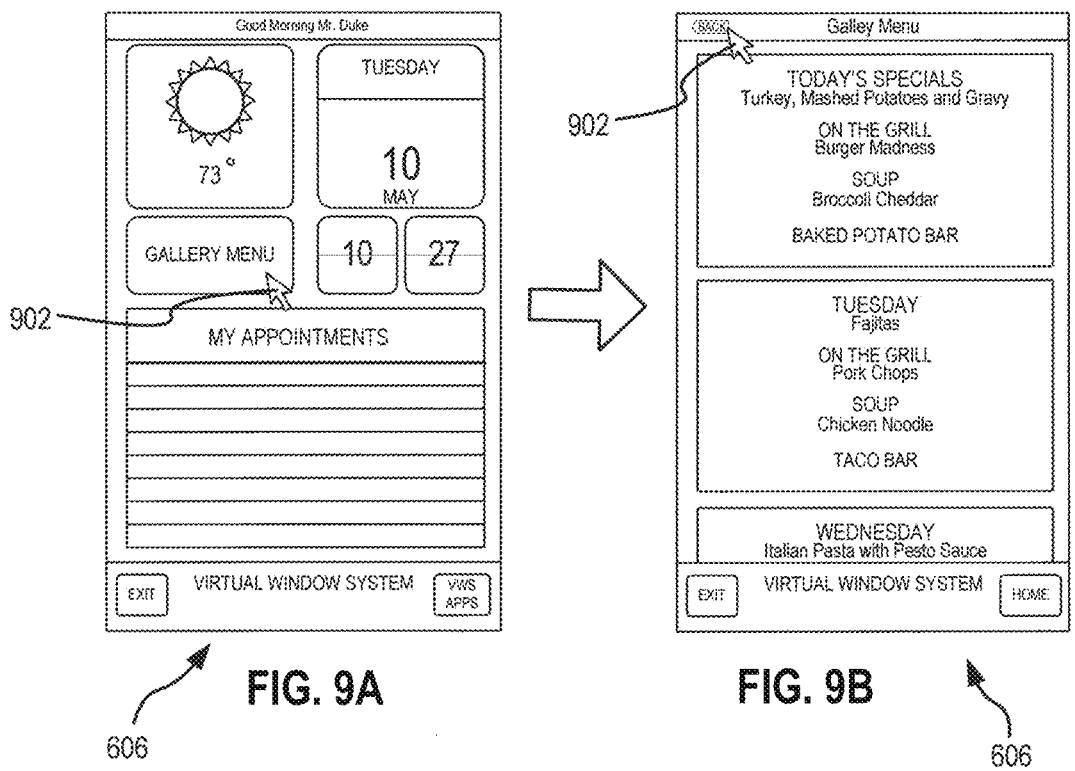
FIG. 9A
FIG. 9B
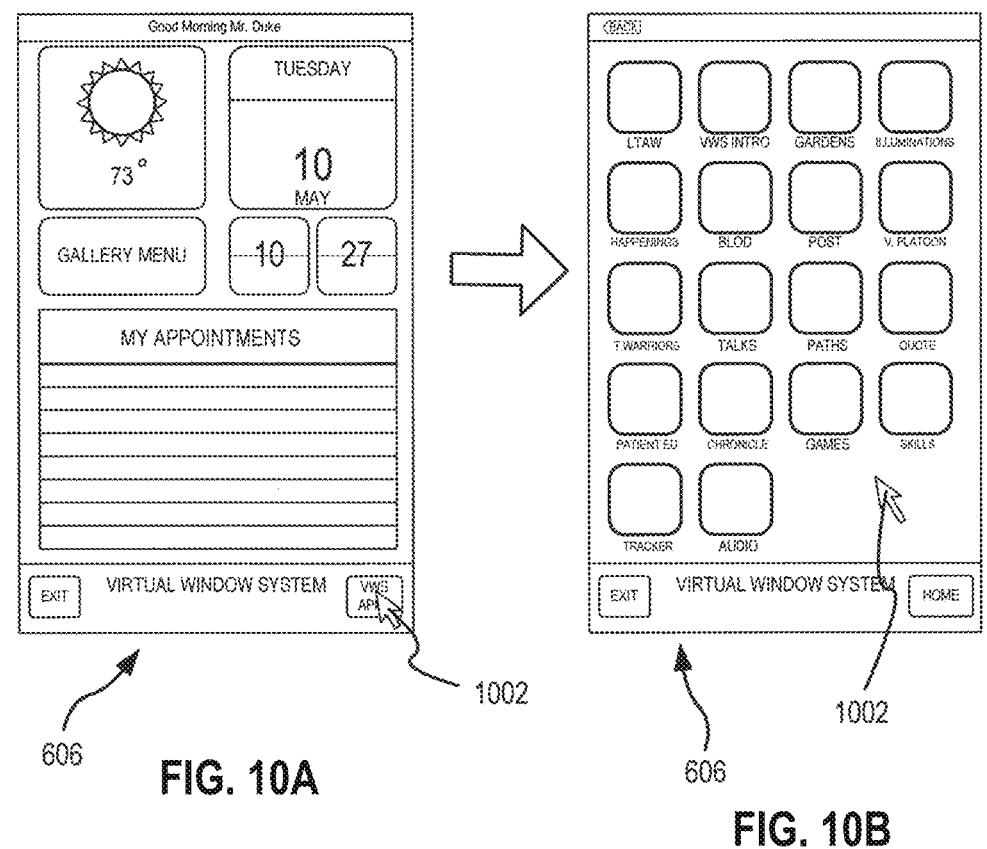
FIG. 10A
FIG. 10B

SYSTEMS AND METHODS FOR AN ADAPTIVE AND INTERACTIVE HEALING ENVIRONMENT

RELATED APPLICATIONS

This application is a continuation of U.S. patent application Ser. No. 15/174,835, filed Jun. 6, 2016, which is a continuation of U.S. patent application Ser. No. 13/748,453, filed Jan. 23, 2013, which claims priority to U.S. Provisional Patent Application Ser. No. 61/589,749, filed Jan. 23, 2012. The disclosures of each of these applications are incorporated herein by reference in their entirety.

BACKGROUND

It is conventionally known that hospital patients, and particularly those who are injured, ill, and/or recovering from surgery, will often heal better and faster when exposed to natural and peaceful environments, such as gardens, or "healing gardens," and the like. Patient healing is also known to improve when the patients have better and more frequent interaction with family members and treatment providers, such as doctors, nurses, hospital staff, and/or caregivers from outside of a hospital itself, or a hospital environment (such as when a patient may be recovering at home). For patients suffering very serious injuries, and/or those requiring long-term care, however, mobility of the patient can be problem where the patient is limited in his or her ability to go, or be brought, to the healing environments. It is also difficult for such patients to spend significant time, and/or interact, with friends and family outside of a hospital environment.

Furthermore, since a typical hospital or patient care facility necessarily has strict sterilization requirements, actual and/or open garden elements, such as greenery or soil, may not be permitted in or near patients or patient rooms. In some situations, access to a natural environment or healing garden is limited not only by facility restrictions or a patient's physical impairment, but also by inclement weather. The healing environments become essentially ineffective to a significant portion of the very beneficiaries for whom they are intended.

Accordingly, it is an object of the present Application to provide systems and methods that render gardens and/or healing environments, or the healing or tribute properties thereof, available or accessible to patients during all seasons, and at all times of the day, regardless of patient mobility.

Accordingly, another object of the present Application is to provide systems and methods that allow natural, healing environments to be virtually brought to patients having limited physical mobility within and outside of a hospital environment.

Accordingly, another object of the present Application is to provide systems and methods that allow greater interaction between patients and their friends and family where physical mobility of the patient is limited.

Accordingly, another object of the present Application is to provide positive and/or constructive ways for patients to spend their "down time" while healing, such as by learning new skills and/or taking active participation in their healing process.

Accordingly, another object of the present Application is to provide external support systems for inspiration, hope, and guidance to patients through the healing process (e.g., messages from and/or stories about amputees who have gone on to become athletes, etc.), as well as positive messaging and forward focus throughout the healing process to enhance the process thereby.

Accordingly, another object of the present Application is to provide "bedside" patient ability to control a room's brightness and darkness, color of room lighting, temperature, and/or audio speaker volume, etc., while also accommodating a patient's personal preferences, which may vary moment to moment, thereby providing a sense of control and empowerment, additional relief, and additional comfort in what may often be considered to be austere surroundings.

SUMMARY OF THE INVENTION

The present system is capable of functioning as a wrap-around extension of a window in a patient's room, or wherever a patient may be, whether elsewhere in a hospital environment, or even at home. The present system may function as a "virtual window" to the outside world, and as an interactive portal for a number of software applications, some of which are described below, and others which can be customized specifically within the present system for the needs of a patient, a patient group, and/or providers and caregivers thereto. The present system is particularly advantageous when the patient is a military veteran receiving medical care, and/or to patients with post-traumatic stress disorder ("PTSD"), traumatic brain injury, burns, amputations, etc., and/or other traumatic or serious conditions that require long-term healing. In addition to providing the enhanced healing environment, the present system may also serve as an emotional tribute to wounded veterans, thereby further enhancing the healing process.

The present inventors thus analyzed and distilled essential healing properties of physical gardens, and then integrated their experimental results into the present system and methods to create a virtual environment for patients to heal more quickly and effectively. Through the present system, patients who would otherwise have little access to natural environments and the outside world are instead exposed to an enhanced virtual environment that has a demonstrably increased soothing, calming, and healing effect on the patient. By being virtually surrounded by, and allowed to observe, nature and natural processes, a patient will enjoy enhanced experiences of regeneration, patience, conservation and economy of resources, metamorphosis, rebirth, propagation, adaptation, perseverance, strength through adversity, and/or growth, among other qualities.

In an embodiment, a system for promoting enhanced healing of a medical patient includes a patient room having accommodations for the medical patient, a central computer connected to a media server, a main display located in the patient room, the main display connected to the central computer and including at least a navigation pane and a content pane, an audio system connected to the central computer and capable of providing sound to the patient room, and a remote unit directly accessible to the medical patient, the remote unit having a capability to control the central computer and a content of the main display and a content of the audio system.

In an embodiment, a method of promoting enhanced healing of a medical patient in a patient room, the patient room including an interactive display and access to a central computer, includes the steps of measuring health-related parameters of the medical patient, recording the measured health-related parameters in the central computer, displaying the measured health-related parameters on the interactive display, and repeating these steps a plurality of times to collect a series of measured health-related parameters over time. The method then includes a step of plotting on the interactive display the series of measured health-related parameters as a chart or a graph.

In an embodiment, a system for promoting enhanced healing of a medical patient includes a patient room including an interactive room display and accommodations for the medical patient, an atrium accessible to the medical patient, an access corridor connecting the patient room to the atrium, the access including a plurality of interactive corridor displays, a central computer capable of networking the interactive room display with the interactive corridor displays, and a remote unit directly accessible to the medical patient, the remote unit having a capability to interact with the interactive room display and the plurality of interactive corridor displays directly, or through the central computer.

In an embodiment, a method of configuring a personal living environment of a long-term patient to promote enhanced healing of the patient comprises providing a central computer controllable via a remote unit. The method includes coupling the central computer to a plurality of output devices and at least one sensor. The plurality of output devices includes displays and speakers. At least one of the displays comprises a navigation pane and a content pane. The content pane is configured to display content selected using any one of the remote unit and the navigation pane. The method comprises arranging the plurality of output devices in the personal living environment. The method includes presenting on the navigation pane patient selectable objective parameters and subjective parameters relating to the patient. The method comprises obtaining an input from the patient, and in response to the input, representing on the content pane a relationship, characterized over a time period, between the subjective parameters and the objective parameters selected by the patient. The method comprises shifting presentation of content from one of the plurality of output devices to another of the plurality of output devices based on a proximity of the patient detected by the at least one sensor.

Additionally, systems and methods according to the present embodiments advantageously may provide a patient with enhanced control over the patient's local environment, including one or more of lighting, window shading, displayed images, sound, communication functionality, entertainment, education modules, health monitoring, and physical therapy and treatment.

BRIEF DESCRIPTION OF THE FIGURES

FIGS. 9A and 9B illustrate an example of a display on the navigation pane, and a selection from the display for menu options, in an embodiment.

FIGS. 10A and 10B illustrate an example of a display on the navigation pane, and a selection to display and access particular software applications, in an embodiment.

DETAILED DESCRIPTION OF THE FIGURES

Figure 1:
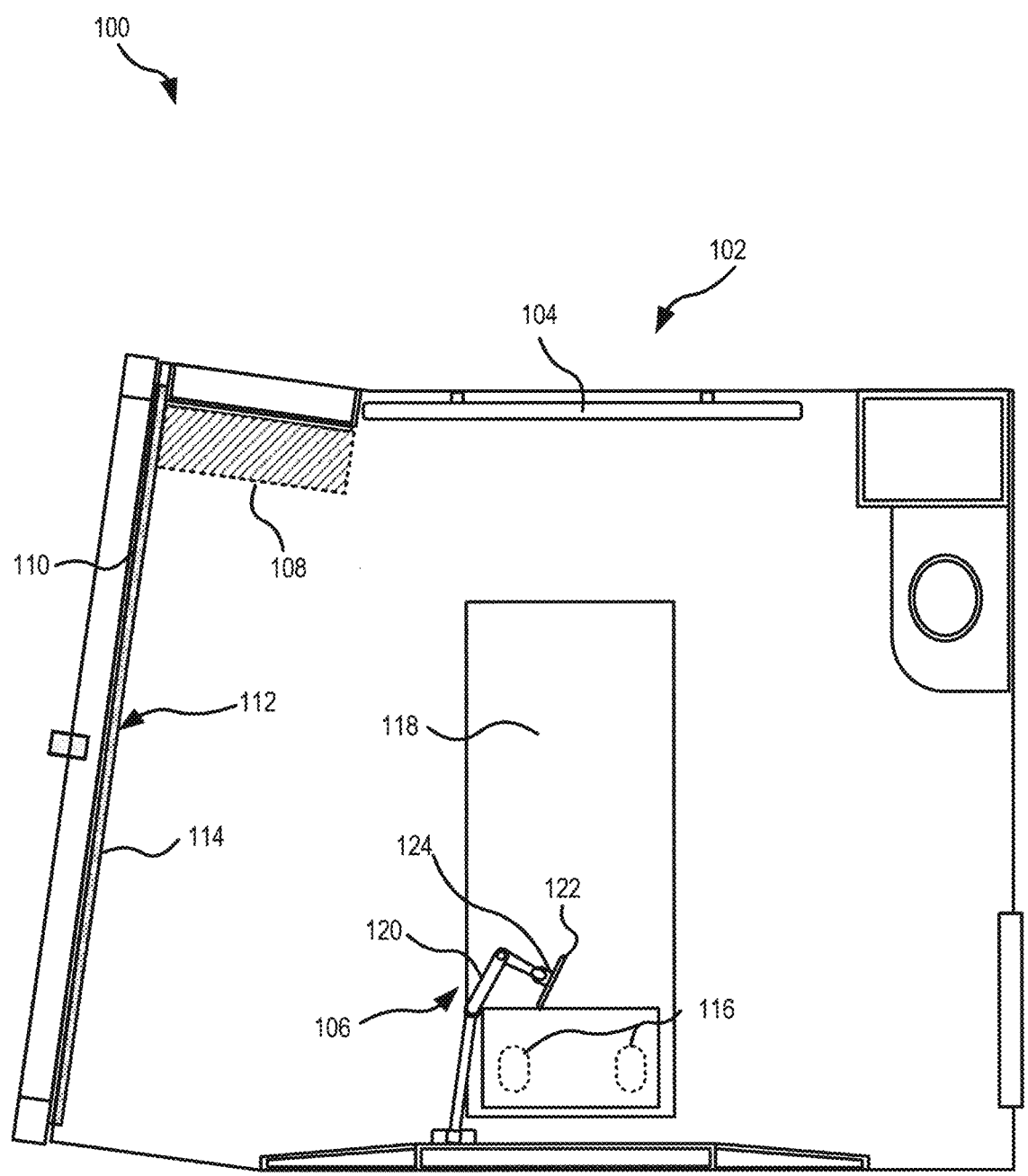
FIG. 1 is an overhead schematic view of a patient room employing the present systems and methods, in an embodiment.
Figure 2:
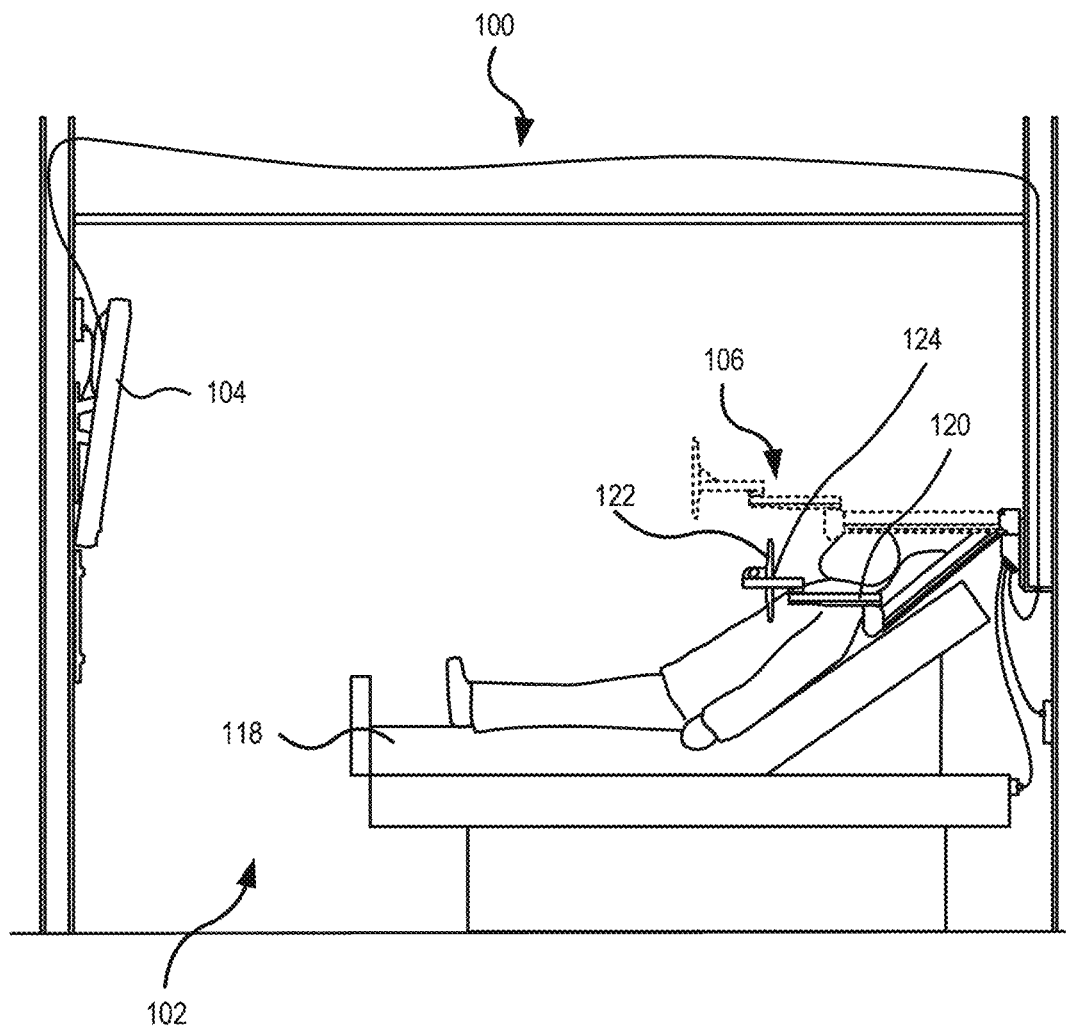
FIG. 2 is a schematic side view of the patient room of FIG. 1.

FIG. 1 is an overhead view of a patient room employing the present systems and methods. FIG. 2 is a schematic side view of the system and patient room of FIG. 1. Referring now to FIGS. 1 and 2, in an embodiment, system 100 includes an enabled patient room 102. System 100 includes a display 104 and a local controller 106. The system 100 may optionally include a desk unit 108 having a dedicated in-room computer (not shown), and/or system 100 may include lighting 110, a window or windows 112, window shading 114, and pillow speakers 116. Lighting 110 can include standard lighting, and/or specialty lighting to provide infrared, ultraviolet, and/or natural light therapy, and lighting. Lighting 110 may be located as a single-source, or spread about the room 102, and can be integrated for remote control by local controller 106. Window shading 114 may be electrically controlled blinds, shades, or the like, and may also be integrated within system 100 for remote control by local controller 106. Pillow speakers 116 should be located in a bed 118, or a headrest (not shown) in a wheelchair (see FIG. 14) or other form of patient transport.

In an embodiment, local controller 106 includes a swing arm 120, a remote unit 122, and a unit holder 124 that connects the remote unit 122 to the swing-arm 120. The swing arm 120 and unit holder 124 hold the remote unit 122 steady for use by a patient, caregiver, or other user. The remote unit 122 serves as a remote control to enable a user to access, use, and/or adjust the system 100 or individual components therein. Remote unit 122 may be hard-wired into the system 100, through the swing arm 120, or connect through the system 100 by other connection means, such as wi-fi or other radio signals, infra-red, ultrasonic, or the like. In an embodiment, remote unit 122 is a laptop computer with a keyboard, or an electronic interactive touch screen component, such as a wi-fi enabled tablet device or a smart phone.

According to an embodiment, the system 100 may be accessed and controlled from a patient bedside with remote unit 122. Unit holder 124 may form protective casing that easily attaches and detaches from swing arm 120 for durability, easy cleaning, and daily disinfecting. Unit controller may also allow for easy docking and release of remote unit 122, such that remote unit 122 may be a dedicated device within the patient room 102, or a patient's own portable device.

The swing arm 120 allows the remote unit 122 to be accessible at all times for patients of all abilities or limitations, and may be easily moved out of the way of the bed 118, to allow access to the patient for patient care, providing food trays, and/or other patient activities. In an embodiment, unit holder 124 may include universal docking features that allow docking and holding of multiple types of control devices (e.g., tablet computers, laptop computers, smart phones of various makes) in the same unit holder 124.

Figure 3:
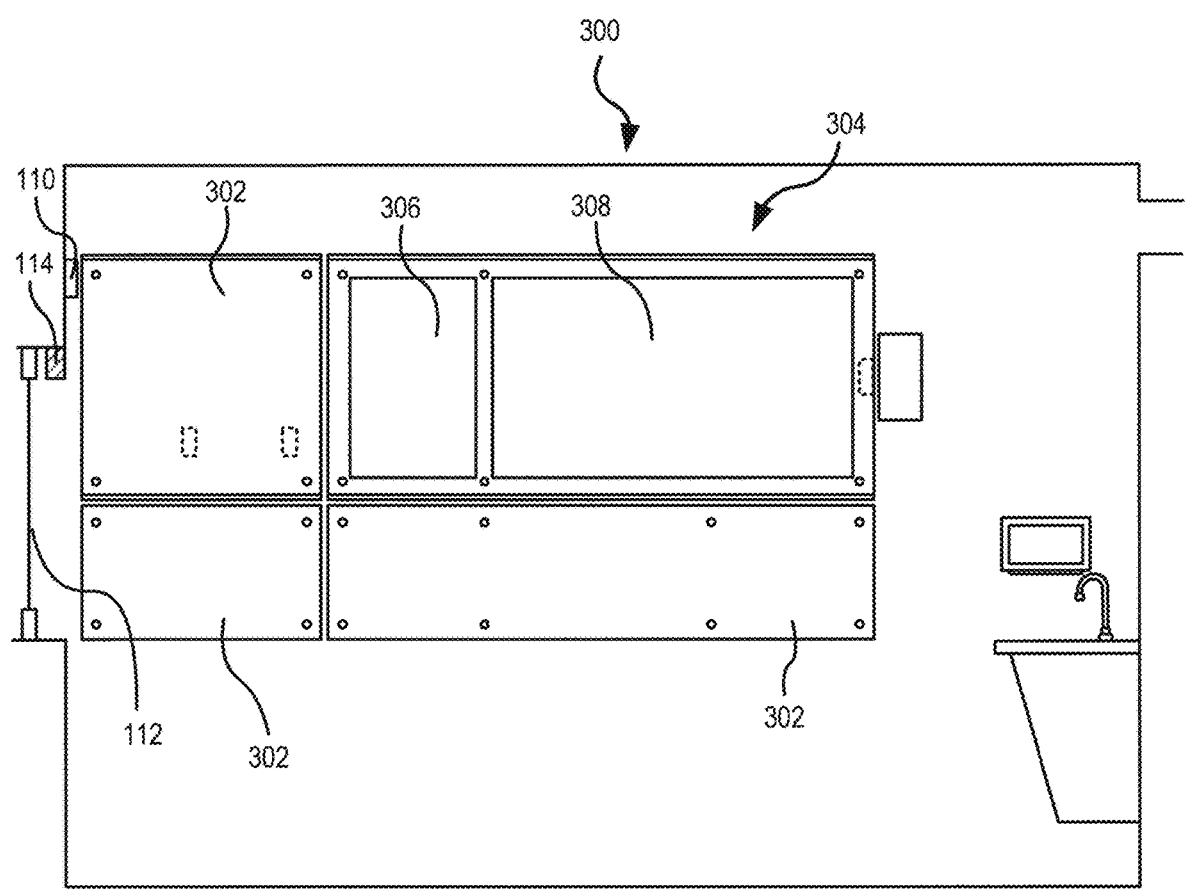
FIG. 3 illustrates some individual elements of the present system, in an embodiment.
Figures 4A, 4B:
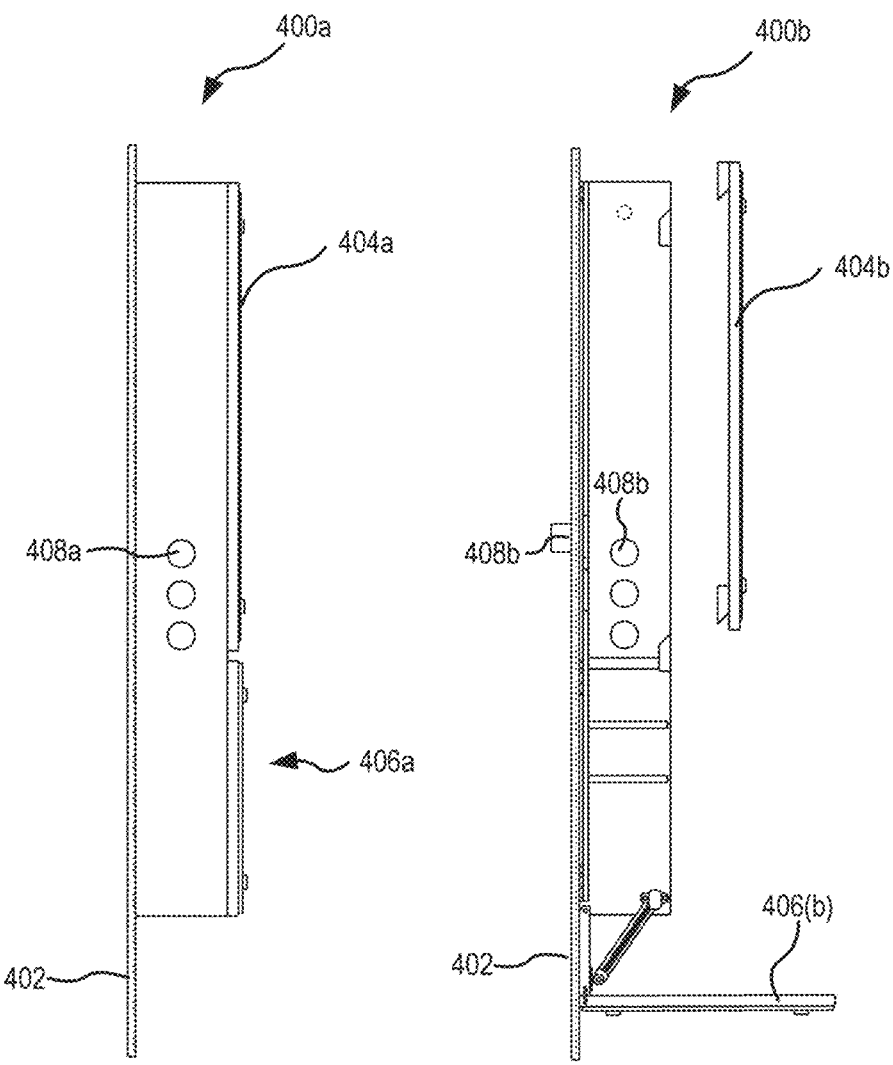
FIGS. 4A and 4B are side views of examples of an assembly for a display as shown in FIG. 3.

FIG. 3 illustrates some individual elements of the present system, in an embodiment. FIGS. 4A and 4B are side views of examples of an assembly for a display as shown in FIG. 3. Referring now to FIGS. 3 and 4, a display 304 may be a stand-alone display device (such as a television or computer monitor, for example), wall-mounted, or integral with a wall (not numbered) of the patient room 102. Display 304 can be a single display screen or a plurality of discrete panels located conveniently with respect to one another. Display 304 may be driven by a dedicated computer (see elements 502, 602, FIGS. 5, 6, respectively), which may be part of a network or a dedicated in-room computer.

In an embodiment, remote unit 122 (FIGS. 1, 2) may be a tablet computer that also may serve as, or operate independently of, the dedicated in-room computer to drive system 100 (FIGS. 1, 2) and display 304 (or 104). Referring back to FIG. 3, an assembly 300 includes display 304 as part of an arrangement together with other personal components 302. Personal components 302 may include one or more of a desk unit (see FIG. 1), a shelving unit, a bulletin board, and an electronics unit, which itself may include a wi-fi router, audio-visual mixers or graphic cards, or other electronic components useful for installing add-on components into the system 100.

In the example shown in FIG. 3, display 304 includes at least a navigation pane 306 and a content pane 308. Navigation pane 306 and content pane 308 may be separate and discrete display panels, or may be distinctly displayed on a single panel of display 304. Navigation pane 306 features navigation controls and menus (see FIG. 6), which can be accessed by remote unit 122 (see FIGS. 1, 2), and may be mirrored in whole or in part on an interactive display (see FIGS. 9A, 10A) of remote unit 122, where remote unit 122 is a tablet computer, a smart phone, or a laptop computer. Content pane 308 features content that may be selected from or by remote unit 122 navigation pane 306, and controlled by remote unit 122 or optionally mirrored in whole or in part on the interactive display (see FIGS. 9B, 10B) of remote unit 122, which may be desirable, for example, if two patients share the same room. Remote unit 122 may itself include various third party and/or custom applications which may in turn be mirrored on content pane 308, and remote unit 122 may also operate as a standalone computer. Assembly 300 and/or remote unit 122 may also include a camera and/or microphone (not shown), for capturing and transmitting images and audio, as part of personal components 302, or personal components 302 may be separate and discrete elements from assembly 300, but still integrated within the operation of system 100

Referring now to FIGS. 4A and 4B, assemblies 400a and 400b are shown, respectively, as fully integrated embodiments of the assembly 300 shown in FIG. 3. In an embodiment, assembly 400a is a fully pre-constructed wall unit that may be plugged into an electrical wall outlet (not shown) and attached to wall 402 as a single unit, and thus easily retrofitted into existing hospital patient rooms (or a wall at a home) where system 100 is implemented, to effectively turn any patient room into an interactive, enhanced healing room. Assembly 400a includes panel 404a and desk/shelf unit 406a, which may be slide-out, fold-down, or swing-open, or a combination thereof.

Other elements of system 100, such as electrical lighting, audio, motorized window shades can be hard-wired into the assembly 400a at input/output connections 408a (or 408b in assembly 400b, FIG. 4B). Input/output connections 408a (or 408b) can also be provided in sufficient quantity and variety to further allow for auxiliary video input, CATV, external video gaming systems and hardware, other hospital equipment and hardware, auxiliary room speakers and audio players, etc.

FIG. 4B illustrates an alternative embodiment for an assembly 408b in system 100. Assembly 408b is similar to assembly 408a, in that assembly 408b is integrally pre-constructed for easy installation/retrofitting into existing patient rooms (or homes). The embodiment of assembly 408b differs from assembly 408a, by allowing for separate installation of panel 404b (and/or individual navigation and content panes, not numbered), and desk/shelves 406b may also be integrated separately as an add-on to assembly 400b according to patient needs and/or room logistics. In an embodiment, panels 404a, 404b can represent removable access panels to allow a user or technician to service, add, or remove components inside the respective assemblies, or display panels that may be added or interchanged as technology improvements allow.

Assemblies 408a, 408b can be sized to be as small as a television or a computer monitor, or be as large as necessary to fill a significant portion, if not most, of a wall facing a patient in bed 118. Additionally, where patient room 102 may not include windows 112, or where windows 112 may be small and insufficient, panels 404a, 404b (or displays 104, 304), or content panes thereof (e.g., element 308, FIG. 3), may be duplicated throughout the room 102 to create a wrap-around extension of the "virtual window" of the patient room 102. This wrap-around effect may function as a virtual window to the outside world—above and beyond what a normal window could provide—and may be the engine for a comprehensive suite of interactive programs designed specifically for the needs of patients, caregivers, and their families/friends. In an embodiment display panels can be attached to motorized lifts to raise and lower the displays over windows 112 of the room 102, to serve a double function of window shading 114. In another embodiment, displays 104, 304 can be display panels that may become completely transparent to all light from windows 112 to completely or partially pass therethrough into the patient room 102 when the displays are not in use, or to include a back layer (not shown) that may become opaque to function as shading 114 block light from the windows 112, and a front layer (not numbered) to display content into the patient room 102.

Figure 5:
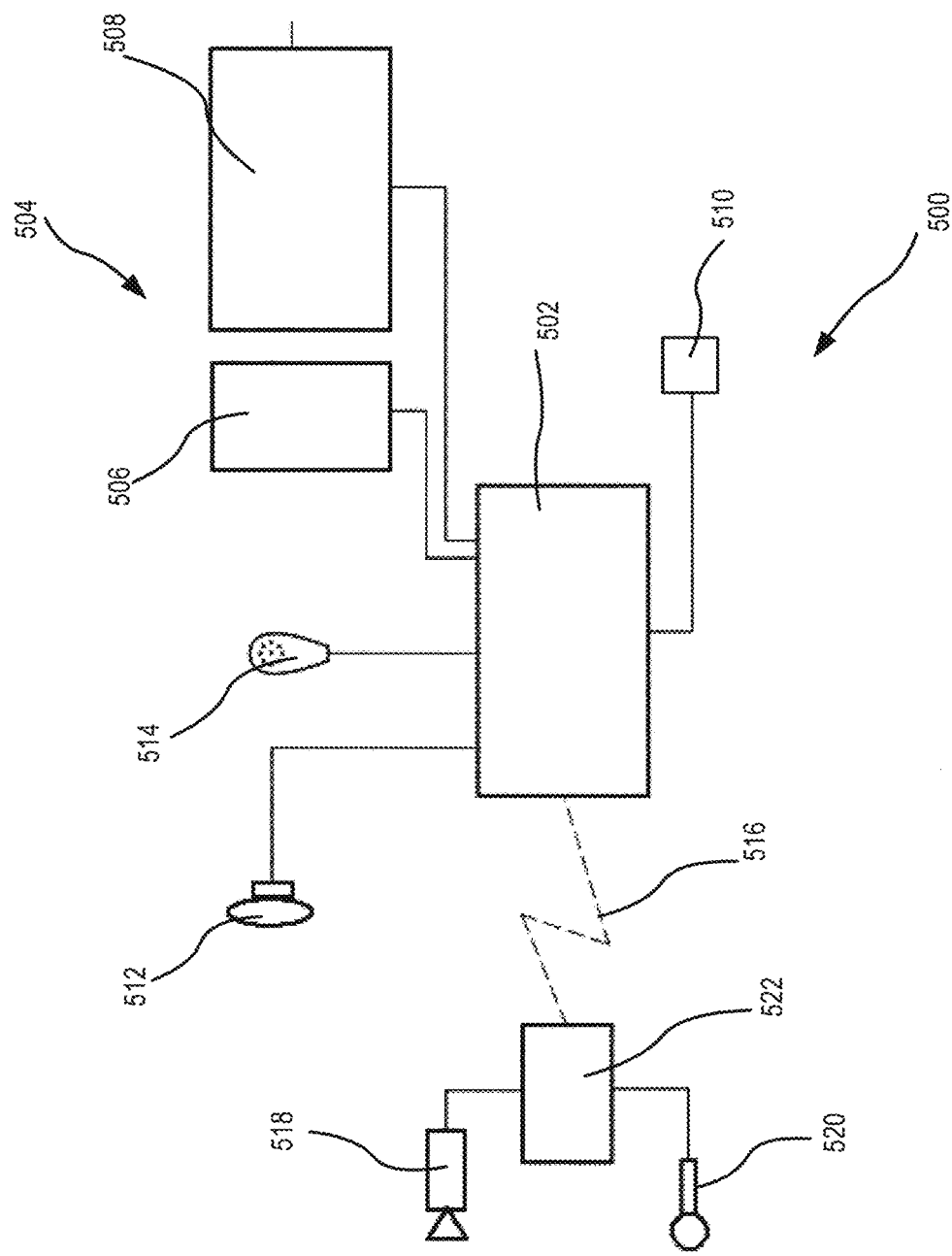
FIG. 5 illustrates a hardware configuration, in an embodiment.

FIG. 5 illustrates a hardware configuration, in an embodiment. FIG. 5 illustrates system 500 as an embodiment of the general system 100 shown in FIG. 1. System 500 integrally includes at least: a central computer 502, which can be a network or dedicated in-room computer; and a display 504, including navigation pane 506 and content pane 508. The central computer 502 may have an Ethernet, or similar, connection 510 to the Internet, media server(s), and/or administrative computers of a hospital network, which servers/networks may incorporate additional patient rooms into system 500. System 500 may further include: external speakers 512, which may be integral to display 504, separate audio speakers, or in-room speakers that are part of a hospital sound system; pillow speakers 514, which could be connected directly to system 500 by hard-wiring or wi-fi connection, such as connection 516, or headphones that plug directly into system 500 or a personal computer; a camera 518; a microphone 520; and a remote unit 522. In an embodiment, remote unit 522 is a tablet-based computer with an interactive screen that allows direct wiring/indirect connections 516 of speakers 514, camera 518, microphone 520, plus other add-on components (not shown).

Similar to the embodiments discussed above, system 500 may feature at least three distinct display surfaces, on remote unit 522, navigation pane 506, and content pane 508. Remote unit 522 may thus be used to select, launch and/or control applications, such as by acting as a virtual mouse and keyboard (not shown). If remote unit 522 is a laptop or personal computer, an actual mouse and keyboard may be used.

Figure 6:
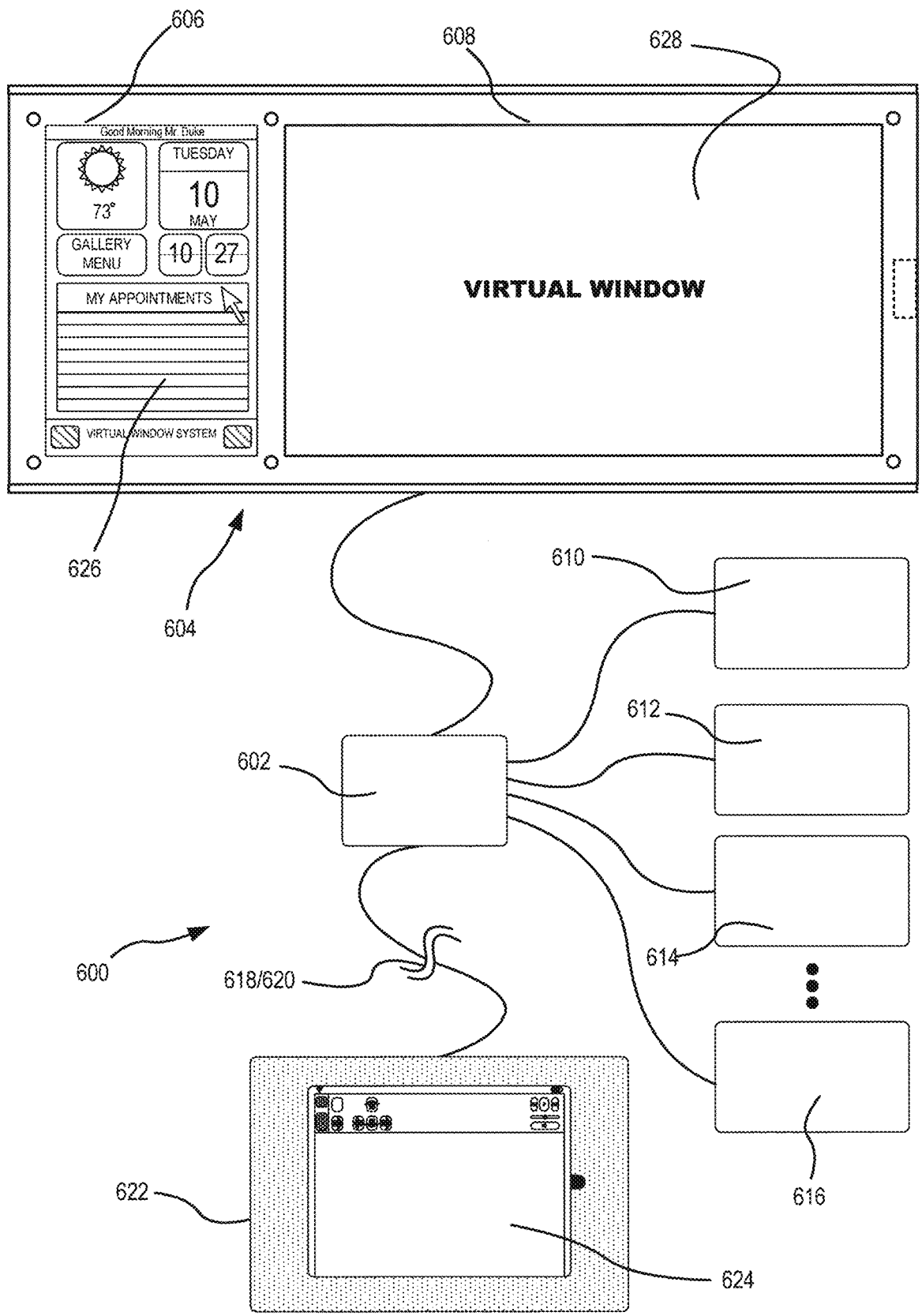
FIG. 6 illustrates a tablet-based user interface configured as a touch screen input to a dual-screen embodiment of the system having at least navigation and content capability, in an embodiment.

FIG. 6 illustrates a tablet-based user interface configured as a touch screen input to a dual-screen embodiment of the system having at least navigation and content capability, in an embodiment. System 600 is similar to system 500 (FIG. 5), with additional focus on management of applications and controls run on and through system 600. In an embodiment, system 600 includes a central computer 602, and display 604 that includes navigation pane 606 and content pane 608. System 600 may further include one or more of audio system 610, lighting system 612, room shading system 614, and environmental controls 616. Connected to system 600 by way of direct wiring 618 or indirect wi-fi connection 620 is remote unit 622. In the example shown in the embodiment of FIG. 6, remote unit 622 is represented as a tablet computer with an interactive touchscreen that displays and controls remote content 624.

System 600 may run system-specific software applications from remote unit 622 and/or software applications installed directly into remote unit 622, or the central computer 602. To activate an application on display 604, a patient or other user may select an icon (not shown) from the remote content 624 of remote unit 622, which in turn may activate an applications menu, thereby turning the remote unit 622 into a virtual mouse and keyboard for navigating wall applications. The user may then use remote unit 622 to select and launch an application from the application menu on navigation pane 606. Such dedicated software applications, activated when launched from remote unit 622, may use display 104 as their primary displays, but may also be mirrored in whole or in part as remote content 624 on remote unit 622. When display 604 is the primary display, remote unit 622 is used primarily as only a controller/mouse/keyboard. Other applications installed on remote unit 622, which are designed to run on remote unit 622, may be selected from remote content 624 and be displayed as part of the remote content locally, or as navigation content 626 on navigation pane 606 and/or as application content 628 on content pane 608.

As illustrated in the example of FIG. 6, navigation content 626 of navigation pane 606 may feature control user interface elements such as menus, buttons, and sliders for controlling application content 628 on the content pane 608, as well as information and descriptions of application content 628. Application content 628 on content pane 608 displays featured wall-based content, such as movies, games, or educational programming. Additionally, system 600 is capable of independently and separately running application content 628 and remote content 624 as distinct software applications, without disconnecting or disabling remote unit 622 from system 600. For example, a movie could be playing as application content 628 on the content pane 608 while email could be accessed from remote content 624 of remote unit 622.

According to this embodiment (as well as other embodiments described herein) system 600 advantageously provides a patient or other user with access to material and content for enhanced self-education, self-healing and rehabilitation, communication, community-building, and entertainment. System 600 further advantageously provides enhanced comfort for a patient/user by allowing easy and immediate control over various aspects of the patient room (e.g., element 102, FIGS. 1, 2) and interaction with the hospital systems, including, but not limited to sound from audio system 610, lighting type and intensity from lighting system 612, quantity of daylight (or privacy considerations) from shading system 614, and electrical motorized operation of a patient bed (i.e., element 118, FIG. 1) or wheelchair (see FIG. 14) or other transport, as well as functionality for ordering food, calling a nurse, making and keeping track of appointments, etc. through existing systems and software applications that can be fully integrated within system 600.

In an embodiment, patient rooms (i.e., element 118, FIG. 1) may include meditative lighting as part of lighting system 612, for which a patient and or caregiver may have control over the brightness and/or color of the light in the room, while shading system 614 can include remote-controlled motorized blinds to similarly control the amount of natural light from windows in the room (or privacy from the outside world). According to system 600, lighting can be further combined with soothing or meditative audio (i.e., through audio system 610) to transform an ordinary patient room into an "oasis of serenity," that is, an environment conducive to healing, relaxation, and body work treatments such as deep-tissue massage. Room lighting control can thus be directly accessed via remote unit 622 (e.g., Remote Control and LED Lighting icons on remote content 624), thereby allowing bedside control of room brightness and color and motorized window blinds.

According to an embodiment of FIG. 6, display 604 may be activated by remote unit 622, and remote unit 622 essentially becomes a remote control, acting as a virtual mouse and keyboard if desired, for accessing and controlling navigation content 626 and application content 628. Operation of remote unit 622 as a remote control device for display 604 is now described.

Figure 7:
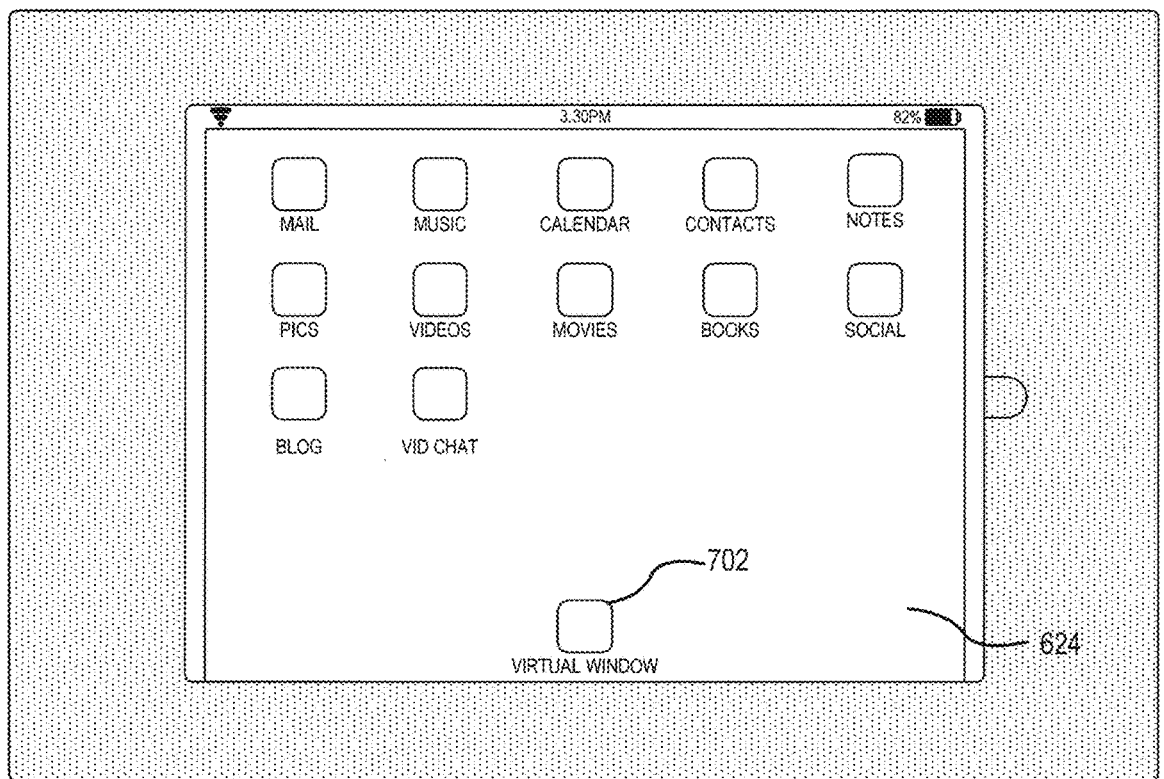
FIG. 7 illustrates an example of a tablet-based user interface system displaying menu content, in an embodiment.
Figure 8:
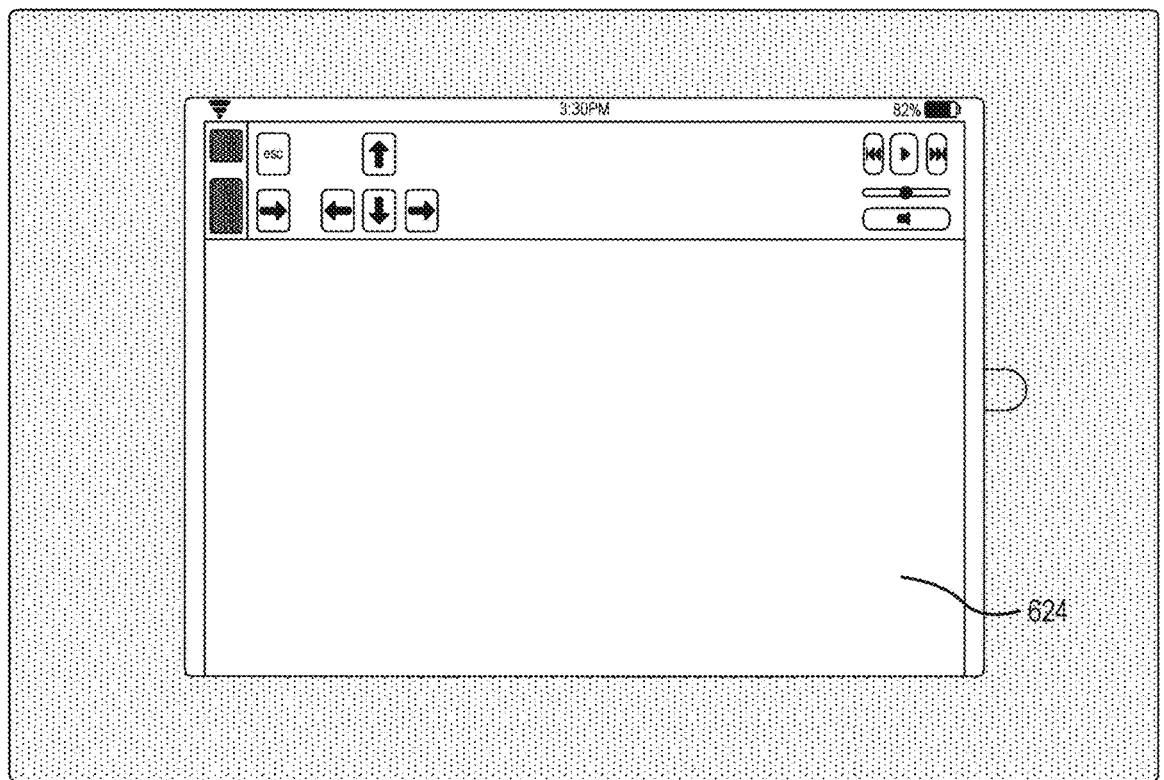
FIG. 8 illustrates an example of a tablet-based user interface system displaying remote control functionality, in an embodiment.

FIG. 7 illustrates an example of a tablet-based user interface system displaying menu content, in an embodiment. FIG. 8 illustrates an example of a tablet-based user interface system displaying remote control functionality, in an embodiment. FIGS. 9A and 9B illustrate an example of a display on the navigation pane 606, and a selection from the display for menu options, in an embodiment. FIGS. 10A and 10B illustrate an example of a display on the navigation pane 606, and a selection to display and access particular software applications, in an embodiment.

As best seen with reference to FIGS. 7-10, applications content 628 (best seen with respect to FIG. 6) on content pane 608 can be controlled through the activation of remote unit 622 as a virtual mouse and keyboard (in an embodiment, specific mouse and keyboard software applications may be provided) by selection of an icon 702 (FIG. 7) displayed on remote content 624. Icon 702 can appear as one of many pre-installed application icons 704, for example, of remote content 624. Once applications content 628 (or navigation content 626) is activated, remote unit 622 effectively operates as a remote control (best seen in FIG. 8) for display 604. On an activated display 604, a home screen may appear on navigation pane 606 (see e.g., FIGS. 9A, 10A), as a user selection, or automatically upon activation. The home screen may include a display of special announcements, current weather conditions, current date and time, galley menus, and/or appointment reminders to be available to a patient or other user at a glance.

Referring now to FIGS. 9A-10B, if a user desires more details about a particular item on the home screen (such as weather, calendars, galley menus, etc.), the user may click a respective icon for the desired item by navigating and activating a cursor 902 shown on navigation content 626. Navigation pane 606 may then update the navigation content 626 (or applications content 628, if desired) with current information on the desired item, either on the same display screen, or by changing navigation content 626 to display a screen dedicated to information about the desired item, as shown in FIG. 9. By activating the "BACK" icon with the cursor 902 in a similar manner, the original home screen may be displayed again for navigation content 626.

Referring now to now to FIG. 10A, from the navigation content 306, a user may similarly navigate cursor 1002 to select a "VWS Apps" (short for "Virtual Window System Applications" in this example) icon of navigation content 626 to alter navigation content 626 (or applications content 628, if desired) to feature a full menu of wall applications, as illustrated in FIG. 10B. Selecting a particular application icon from the menu of wall applications may launch the selected application for display as application content 628 on content pane 608, controlled by remote unit 622. Similar to the example shown in FIG. 9b, selecting "Back" with cursor 1002 from navigation content 626 may return navigation content to the wall application menu (FIG. 10b) or the home screen (FIG. 10a). Selecting the "Home" button toggles the navigation pane back to the Home screen. In an embodiment, navigation content may include an "Exit" icon, the selection of which by cursor 902/1002 may power down display 604 and return remote unit 622 to its regular, non-system functioning, e.g., as a tablet computer.

Among many software applications that have been specially created by the present inventors for running on one or more of the several display screens of system 600, are the following: nature applications and motion pictures ("Gardens"); lessons from nature ("Illuminations"); an electronic bulletin board ("Happenings"); a private patient/wounded soldier blogsite ("Blogsite"); specialized e-greetings ("Post"); a custom social network to keep a wounded soldier in contact with his unit, superiors, and command ("Virtual Platoon"); stories of other users, past and present, particularly those with conditions/experiences similar to the patient/user ("Time Warriors"); motivational talks and films ("Talks"); lessons or live interaction with life coaches and guides ("Paths"); a quotation screensaver, which may be set to run while display 604 is powered down ("QuoteSaver"); personalized patient education lessons and classes ("Patient Ed"); a personal progress log ("Log"); virtual games and interactive entertainment specifically suited for patient recovery and morale ("Games"); skill building modules, particularly for injury rehabilitation and new job training ("Skills"); a personal medical tracking program ("Tracker"); and a meditative audio program and selection designed for a particular condition or needs of the patient ("Audio Oasis"). Many of these specialty software programs are described in greater detail further below.

In addition to the software applications, some described above, created by the present inventors for specific use with the present systems and methods, the present inventors have also advantageously designed the system 600 (or 100) to seamlessly run one or more of the following known software applications as one or more of the many menu application selections available from remote content 624 of remote unit 622: email; audio/video chat; MP3 music library and player; DVD, MPEG, Flash video library and player; ebook reader, library, and/or player; personal digital calendar; personal electronic directory; personal digital photo library; digital notepad; application store to purchase and/or add further software applications within the remote unit 622 or system 600; publicly available digital and virtual games.

System 600 may further be adapted to include icons for easy access to the following additional features that a hospital patient may desire to be able to access directly from remote content 624 (or navigation content 626 or applications content 628, controlled by remote unit 622): electronic window blind/shading activation and control; room lighting control; picture display control (voice over, zoom, color/black-white intensity or contrast, etc.); closed captioning and subtitles; dictation programs and language recognition; and stylus programming to more easily operate the interactive touchscreen of remote unit 622.

With respect to the Gardens application, patients can gain virtual access to nature via a "Living Gardens" nature video series, for example. The Gardens application is thus a serene but powerful feature of system 600. The significant advantages achieved through utilization of the Gardens application may be understood by one who has had to spend considerable periods of time removed from a natural environment, and then has to go through an extended healing process. The present inventors have discovered that a patient's need for an experience of natural surroundings becomes more highly pronounced when it has been absent for a length of time, and can be met to an extent by being virtually brought to the patient through use of the Gardens application.

The nature videos that are part of Gardens have themselves been designed with particularity by the present inventors to serve as an inclusive device, that is, one that connects and virtually surrounds a bed-bound patient with a virtual natural world that the patient would normally be unable to personally access. The Gardens application thus serves as a further motivational incentive for bed- or room-bound patients who are unable, but may be able at a later time, to progress during their hospital stay to one day make it to a dedicated hospital garden. Nature films that are accessible from the Gardens application may include customized video footage created especially for system 600 (or 100) and patients, and also selected publicly available video footage from third party sources. In an embodiment, effects from this application (as well as several others described herein) can be enhanced by increasing the size of display 604 to cover a significant portion of a wall—or several walls—on which display 604 is located.

With respect to the Illuminations application, patients can experience a suite of nature-themed videos with subtle embedded and implied stories and lessons, to inspire and give a sense of belonging to the world, for patients who undergo an extended healing journey. The present inventors have discovered that nature has many lessons to impart to attentive patients about persistence, growth, evolution, change, adaptability, and survival, to name just a few. Caregivers often overlook the fact, especially in a sterile hospital environment, that people are a part of nature too. Human beings, as well as flora and fauna, live according to nature's laws and share in its bounty. More particularly, the present inventors have discovered that, to enable understanding of natural processes that are sometimes invisible to urban audiences (especially patients who may have been raised somewhat removed from natural environments), it can be advantageous over conventional methods and systems to better utilize media and interactive methods to make such natural processes visible and at real scale, when such processes are not often fully visible in real time.

Some nature lessons of the Illuminations application may include one or more of the following examples: (1) after a time of dark, isolated waiting and change, a caterpillar becomes a butterfly; (2) a seed pushes its way through dark earth in order to break through to light; (3) various aspects of nature going through dependable cycles of growth, death, and rebirth; and (4) various living organisms experiencing and requiring rest and downtime, hibernation, or vernalization. Lessons for the Illuminations application may be accessed by selecting an "Illuminations" icon on a menu displayed on one or more of remote content 624, navigation content 626, and application content 628. The present inventors have designed the Illuminations application to include customized video footage created especially for system 600 and particular patients who will utilize system 600, as well as selected video footage from third party sources. The Gardens and Illuminations applications can be set to run when selected by a user, or automatically according to needs and desires of a particular patient or user.

System 600 not only enhances a patient's desirable time for quiet and solitude by implementation of applications like those discussed above. The present inventors have created system 600 to further integrate for a patient time and capability for socialization and community. System 600 advantageously allows patients to maximize benefits from both solitude and socialization. Patients who are bedridden will usually have ample time for solitude (although such time is not often effectively utilized by caregivers), but often require assistance to access socialization avenues beyond visitors to their patient rooms or the hospital facility in general.

Isolation while suffering through a difficult and/or prolonged healing process can quickly result in a feeling of despair for a patient, which negatively affects the patient's ability to heal. Studies on trauma patients show that those who isolate themselves, or become isolated by circumstance, fare much worse than those who share their experience with others and remain part of a larger community. The present inventors have thus created system 600 to advantageously include features and applications for communication tools by which patients can reach out to or be more easily reached by friends, family, colleagues, and other patients within and without the hospital environment, thereby creating and maintaining important personal and community ties.

One such communications tool is the Blogsite application created by the present inventors. The Blogsite application features a private blogging network reserved strictly for injured soldiers (often referred to as "Wounded Warriors") on one of the content menus, described above, for system 600. The present inventors have recognized that many injured soldiers are still on active duty status, and may still be subject to significant security restrictions. Furthermore, many recovering soldiers or veterans who have been honorably discharged from the military may still benefit greatly from communicating with other military personnel who may themselves still be actively deployed and subject to security restrictions in communications. The Blogsite application is specifically created by the present inventors to allow communication with recovering soldier patients, while appropriately addressing security concerns of the military, as well as privacy concerns of the medical environment.

Similar to the applications described above, the Blogsite applications may be accessed by selecting a "BLOG" icon, for example, from one of the content displays (624, 626, 628) of system 600. In addition to the security and privacy concerns, described above, the private blogging network further provides a safe place for Wounded Warriors to post anything that they would like to share within the particular community without concerns of judgment by or lack of understanding from outsiders unfamiliar with issues particular to Wounded Warriors. The present inventors have discovered that the ability to communicate with and relate to other Wounded Warriors through system 600 can be a major factor in the healing process for Wounded Warriors who experience a sense of alienation from the outside world. Utilization of this application can be of particular benefit to Wounded Warriors suffering from PTSD.

The Blogsite application, running on system 600, may include at least the following features: an ability to create a blog page using text, audio, and video clips, similar to existing blog sites open to the public; a "Private Warrior" blog community, closed to the public; an ability to view blog pages from others in the private community; an ability to comment on other's blog posts within the community; a community page (similar to conventional social media sites) which may feature current posts; availability of the site to other Wounded Warriors within and without the particular hospital environment of a single patient; and an ability to create an "avatar" as a virtual representation of the Wounded Warrior.

Another communications tool provided by system 600 is an integrated access to email, from at least a default email client for the remote unit 622 (if remote unit 622 has internal email client capability), to any or all of a patient's other existing email accounts, if so desired by the patient. The present inventors have discovered that patients—and especially Wounded Warriors—are often transferred from facility to facility throughout their healing journey, and "regular" mail can take a while to catch up to the patient. The bedside email access provided by system 600 makes sure that the patient can stay connected to friends, family, fellow Wounded Warriors (if applicable), and the outside world, with the state-of-the-art communications tools and applications provided by system 600.

In an embodiment, email may be accessed directly from remote unit 622, and displayed on display 604 if desired. The Email application of system 600 may further include, when selected: its own home screen; a default email client for remote unit 622; easy, integrated access to external web mail accounts; security/filtering (internal or by a third party) based on hospital (and/or military, if applicable) standards and regulations; an ability to send, receive, and save photo and video attachments; and an ability to send, receive, and save attachments; specialized security and file storage management.

In addition to the email applications, described above, the present systems and methods further may allow a patient access to online chat using text, audio, and video, through remote unit 622 and or display 604, available at the patient bedside. A webcam and microphone, for example, may be integral to either remote unit 622 or display 604, or both, or may be integrated within system 600 as separate, discrete components. Soldiers on a battlefield are now known to use online, real-time tools to communicate with friends and loved ones, often considering such communication to be the soldier's "lifeline" to home. The present inventors have discovered that hospitalized Wounded Warriors may greatly benefit, with respect to the healing process, from access to that same "lifeline."

In an embodiment, system 600 is further capable of providing a Chat application that may be accessed directly from remote unit 622, and/or utilized together with display 604, as well as other audio/visual components integrated with system 600. The Chat application may have its own home screen, which may be accessed by selection of a "Chat" icon on one of the several content screens of system 600, and may further feature: easy, integrated access to third party chat applications; plug-in capability for an external keyboard (as well as a virtual keyboard on remote content 624); plug-in capability for an external webcam and/or microphone (or use of such built-in hardware as may be found in examples of remote unit 622 and/or display 604); and filtering and security compatibility with hospital and/or military administrative and technical approval and support.

With respect to the Post application, patients are able to, through system 600, create and send letters and greeting cards from their bedside, in addition to greetings that may be sent through regular email channels. Traditional mail has a tendency to be slow, or even become lost, for patients requiring extended healing time at one or more hospital facilities. This problem is particularly pronounced for Wounded Warriors within the military medical system, precipitating a need for a reliable and timely tool for sending greetings. The Post application of the present system, however, allows patients personal touches and creative outlets, such as the ability to make and send virtual or physical personalized greeting cards. The present inventors have discovered that this ability for patients may provide additional relief from long periods spent in a clinical setting, and can tap into the heart-to-heart connection with friends and loved ones that further enhances the overall process of healing.

Similar to the applications discussed above, the Post application can be accessed by a patient by selection of the relevant icon from one or more of the several content screens of system 600. The application may include one or more of the following features and abilities for patients: send and receive e-greeting cards and save such virtual cards for later display in application content 628; send e-greeting cards from a library of pre-made cards stored within a memory of system 600, with ability to add signatures, custom text, and/or personal photographs and images; create and send customized e-greeting cards using templates of background colors, patterns, and images; and secured access to third party greeting card companies to send physical greeting cards through the third party system. The application may run on a local server, and may send greetings through regular mail and email channels.

System 600 further allows patients, with respect to the Happenings application, to learn and keep apprised about events at the hospital and/or within the hospital gardens by accessing a customized electronic bulletin board created by the present inventors. In addition to alerting a patient about such events, the Happenings application further has the capability to connect the patient to cycles of nature, natural processes that may be happening in real-time outside in the gardens that the patient may not yet be able to access, and to what may be expected to unfold over the cycle of the seasons.

The Happenings application may also act as a default screen for display 104, or upon logging in to the system, and the Happenings application may provide the patient with a greeting for the patient, providing updated information on weather, events, and general or specific announcements. Similar to the applications discussed above, the Happenings application can be accessed by a patient by selection of the relevant icon from one or more of the several content screens of system 600. The Happenings application may include and provide one or more of the following features: information on hospital or garden events, upcoming visitors or speakers, outings, recreation, food, and/or local festivities; special announcements; and a capability for patients to customize a home page for the application according to the patient's personal interests and viewing preferences.

Figure 11:
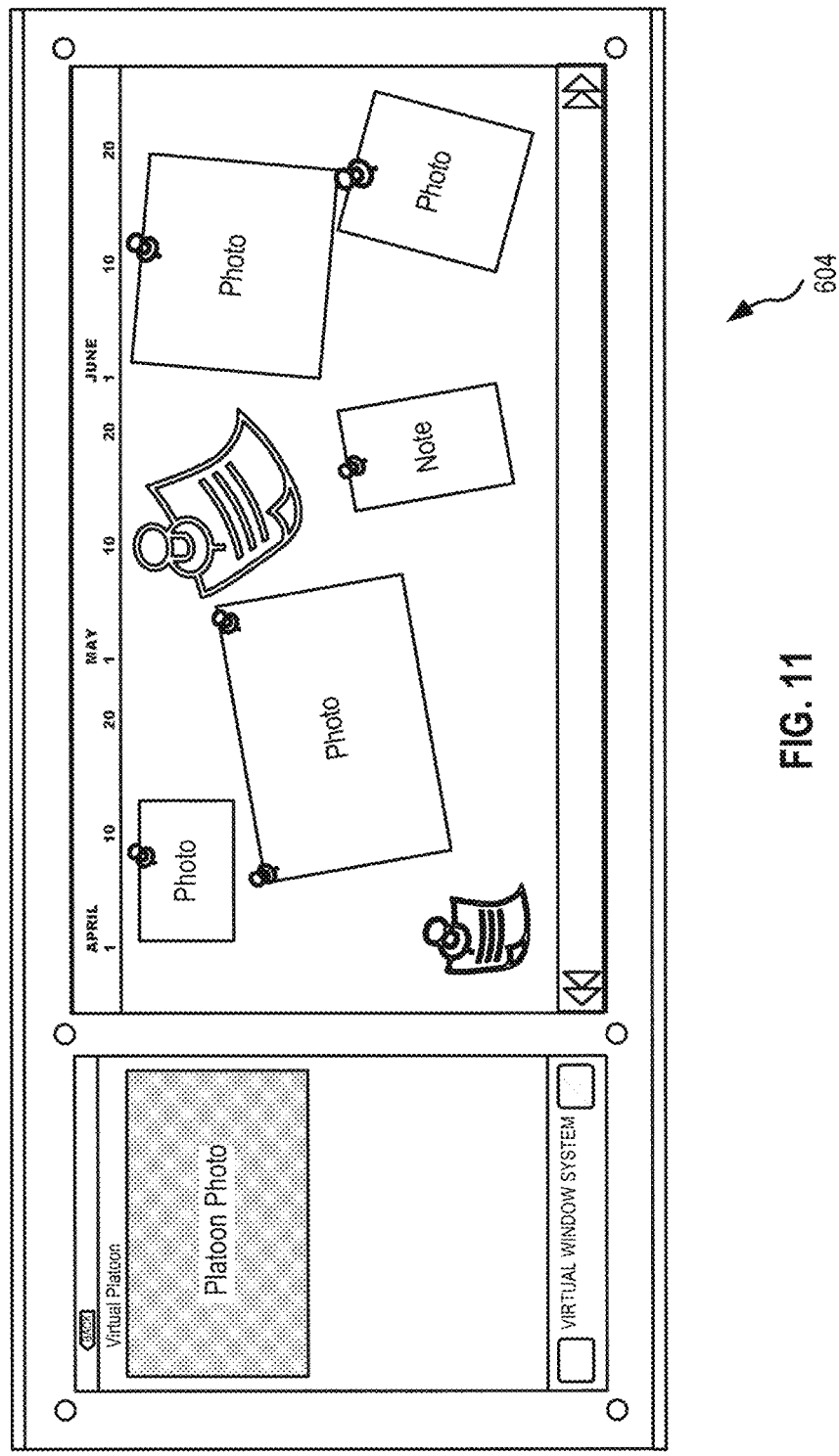
FIG. 11 illustrates a display and use of a particular application selected from the applications shown in the example of FIG. 10B, in an embodiment.

FIG. 11 illustrates a display and use of a particular application selected from the applications shown in the example of FIG. 10*b*, in an embodiment. With respect to the Virtual Platoon application, Wounded Warrior patients are provided a message center dedicated specifically to members of the U.S. Armed Forces who want to keep in touch. The Virtual Platoon application may thus serve as a global digital community bulletin board where servicemen and women can post text, images, audio, and video within the larger service community. It can be too easy for hospitalized or recuperating soldiers to be separated from their units by more than just time and space. Through the Virtual Platoon application, the present system allows a greater opportunity for a Wounded Warrior to remain a part of the military community.

Similar to the applications discussed above, the Virtual Platoon application may be accessed by a Wounded Warrior patient by selection of the relevant icon from one or more of the several content screens of system 600. The application may include one or more of the following features and abilities for Wounded Warriors: view text, image, audio, and video posts by others, particularly in their, or their former, military unit(s); upload text, image, audio, and video posts; and scroll through past postings along a timeline.

Through several other applications created by the present inventors, the present system may also offer patients the ability to hear and view inspirational stories and guidance from fellow soldiers past and present (in the case of Wounded Warriors), motivational speakers from various backgrounds and cultures, as well as religious, spiritual, and/or philosophical guides and coaches.

Returning now to FIGS. 7-10*b*, where the patient is a Wounded Warrior, through the Time Warriors application, system 600 allows the patient the ability to watch and listen to fellow soldiers, past and present, who have stories to tell about their experiences of overcoming difficulties during and after wartime. While there are many differences in any one soldier's experience, there are also a multitude of similarities that can offer insight, guidance, solidarity, and hope to a Wounded Warrior patient.

Similar to the applications discussed above, the Time Warriors application may be accessed by a Wounded Warrior patient by selection of the relevant icon from one or more of the several content screens of system 600. The application may include one or more of the following features and abilities for Wounded Warriors: videos of soldiers or military personnel, past and present; wartime stories; post-war stories; POW stories; and selected third party videos and other content.

The Talks application of system 600 will also allow patients to watch and listen to stories and speeches from people from all walks of life, within the military and without, who have motivational messages to offer. Inspirational words from a fellow human being can often be a single motivating factor to inspire a patient to fundamentally desire to cooperate in their own healing process.

Similar to the applications discussed above, the Talks application may be accessed by a patient by selection of the relevant icon from one or more of the several content screens of system 600. The application may include one or more of the following features: customized video footage created especially for system 600, patients, and/or Wounded Warriors; and selected video footage from third party sources.

The Paths application of system 600 will allow patients access to a library of lessons, exercises, and programs by a variety of different types of spiritual guides and/or life coaches. Regardless of spiritual background, each patient should be able to find a guide to which he or she can relate.

Similar to the applications discussed above, the Paths application may be accessed by a patient by selection of the relevant icon from one or more of the several content screens of system 600. The application may include customized modules created especially for system 600, patients, and/or Wounded Warriors, as well as selected modules from third party sources.

The QuoteSaver application of system 600 will allow patients a direct and efficient way of "speaking" to someone by way of exposure to short and succinct, but very powerful and important, messages from others who have experienced significant difficulties in life. In an embodiment, the QuoteSaver application may feature a quotation screen saver that may softly appear and fade away in a tranquil rhythm, thereby providing quiet and continuous messages of inspiration and hope to the patient. The application may be set as a default screen saver for display 604, or may be activated by selecting the relevant icon from one or more of the several content screens of system 600. In addition to providing cycling text quotations that may slowly fade in and out, the application may also allow the provided text to slowly change text and background color as well.

The Patient Ed application of system 600 will allow patients to take a significantly more active role in their own healing process. Often, patients with intense and stressful injuries or illness are only capable of putting their energies into healing and making it through each day. Eventually, however, some patients may need or want to learn more about their condition and the things that they (or a family member) can do to more actively care for themselves. An understanding of the physiology of one's own medical condition—especially in the case of such complicated conditions as PTSD—may often transform a patient from a helpless, hopeless victim to an empowered, active participant in his or her own healing process. For example, the knowledge of why a particular physical therapy or balancing exercise may be necessary might provide the patient with the necessary motivation to execute the therapy, and/or work harder at the therapy.

Learning about and comparing various treatment options can also be directly empowering for a patient, especially where self-application of treatments may be possible, e.g., trigger point massage for amputees, mind/body exercises for traumas and PTSD, etc. Family members and home caregivers, who are often required to care for a patient once the patient leaves the hospital environment, may also benefit from easy access to organized, user-friendly, non-clinical, and ongoing care information, as well as updates on treatments and procedures as they become available.

Through the Patient Ed application of system 600, patients, family members, and caregivers can receive personalized medical information that pertains to the particular condition(s), care, and treatment relevant to the patient. The Patient Ed application provides simple information, courses, and/or "mini-lessons" on various topics about, and related to, medical conditions and their treatment. By accessing this application, patients may learn about ongoing and follow-up care that may be employed by the patients themselves (or their caregivers), both in the hospital environment and at home or elsewhere.

The present inventors have created the Patient Ed application to complement and enhance, but not replace, medical treatment and advice provided by a physician and/or hospital facility. The Patient Ed application allows for information provided thereby to be first fully vetted and organized by hospital clinical staff. Furthermore, access to various courses and information of the application may be specifically tailored for a particular patient as desired by clinicians and caregivers. In an embodiment, the application may also allow patients the ability to rate courses and make comments as desired, in order to compare notes on what others have found helpful, or not so helpful.

Similar to the applications discussed above, the Patient Ed application may be accessed by a patient (or caregiver) by selection of the relevant icon from one or more of the several content screens of system 600. The application may include one or more of the following features: a personalized syllabus of medical information and "mini-lessons;" text, audio clips, video clips, and interactive content; customize and selected third party content; an ability to rate and comment on courses taken through the application; an ability for hospital staffing resources to assign content to particular patients as desired; and capability for integration with a hospital facility's learning management system.

The Log application of system 600 will also allow patients to track their healing journey as desired, or as they are able. In an embodiment, the Log application may be a personal log, or journal, as opposed to a public blog. Through use of this application, a patient may make as many entries as the patient would like, and on any day the patient chooses. A patient may then view previous entries as desired at a later time, individually, or grouped as part of an overall timeline. A patient using this application may also select iconic images that illustrate the patient's feelings for a particular entry.

Similar to the applications discussed above, the Log application may be accessed by a patient by selection of the relevant icon from one or more of the several content screens of system 600. The application may include one or more of the following features and abilities for the patient: new log entries may be added daily, or several times a day; log entries may updated throughout a day; text and embedded images may be added or attached to each entry; and iconic images may be selected to illustrate feelings experienced at the time of a particular entry.

Figure 13:
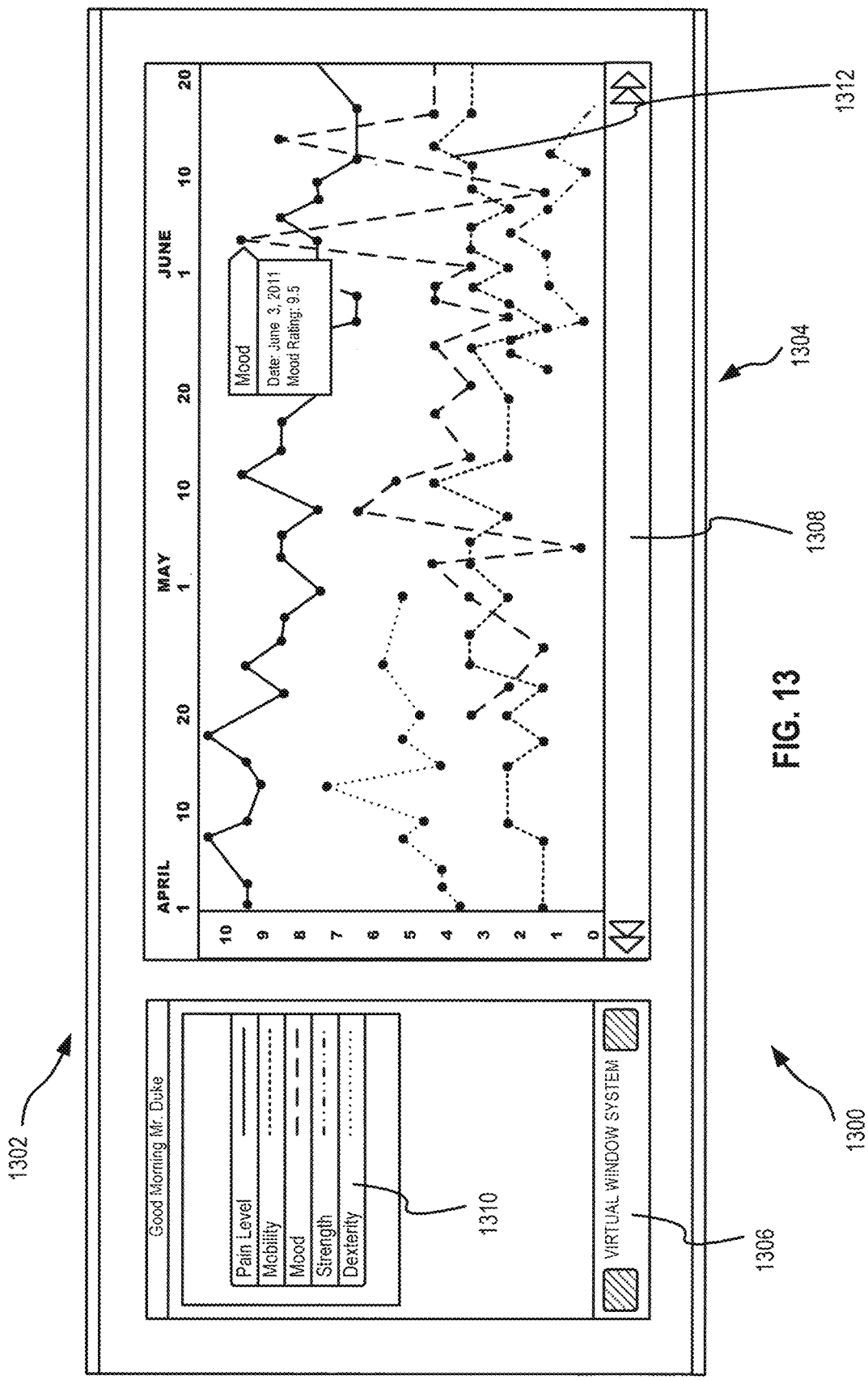
FIG. 13 illustrates a display and use of another particular software application, in an embodiment.

FIG. 13 illustrates a display and use of another particular software application, in an embodiment. In the example shown in FIG. 13, system 1300 is shown to display an operation of a personal tracking application 1302 on display 1304, for tracking a patient's physical, mental, and emotional health. System 1300 can be considered, for purposes of this example, to function and operate similarly to systems 100, 600, described above, and display 1304 is likewise comparable with displays 104, 304, 604, also described above.

According to the example illustrated in FIG. 13, Tracker application 1302 of system 1300 will allow patients to plot and view, on display 1304 (or remote unit 622), the patient's personal healing progress over time. In an embodiment, the patient may select, for display on navigation pane 1306, for example, particular parameters 1310 (e.g., pain level, mobility, mood, strength, dexterity, etc.) to monitor and then display, on content pane 1308, for example, the progress of parameters 1310 as one or more graphs 1312. Optionally, progress displayed by Tracker application 1302 may also be coordinated and superimposed with physical health readings of the patient (e.g., blood pressure, pulse, blood enzymes, temperature, etc.), to provide a comparison of subjective parameters 1310 of the patient with objective physical measurements.

When interred in a hospital room for long periods of time, for example, it can be difficult for patients to see or feel any progress in the patient's healing journey, irrespective of objective health readings. Pain and debilitation may divert the patient's attention and energy to the present moment only, and away from future healing progress, which can feel hopeless to a patient at times, thereby adding a risk of experiencing despair and depression, which can negatively affect the healing process that is specifically sought. According to Tracker application 1302 though, a patient can visualize on display 1304 positive healing progress that the patient may not be feeling at the moment, and thus increase the likelihood of recovering a positive attitude and energy to further contribute to their own healing process. In an embodiment, patients may be able to take the data with them after leaving a hospital setting.

Similar to the applications discussed above, Tracker application 1302 may be accessed by a patient by selection of the relevant icon from one or more of the several content screens of system 1300. In an embodiment, the application may be fully customizable. The patient may be able to enter and track particular information and parameters 1310 as desired, thereby creating personally-customized graphs 1312 for viewing on content pane 1308 of display 1304. Optionally, each graph 1312 can be viewed separately or together with other graphs 1312, in order to gain a perspective of comparative viewing. Additionally, Tracker application may include one or more of the following features and abilities for the patient: create and define graphed items 1312; plot daily entries for each graph 1312, by entering a 1-10 value, for example, for each entry; create and save comments for each entry; turn viewing on and off for each graph 1312 to view separately or comparatively on display 1304; view previous entries by selecting specific points on a graph 1312; and superimpose graphs 1312 and individual entries with objective physical health readings of the same patient.

Aside from medical conditions, the present inventors have found that boredom is the second highest complaint (isolation being the first highest complaint) from patients—and particularly Wounded Warriors—who are hospitalized for a significant length of time. According to the present systems and methods though, patients may advantageously receive an enhanced experience of recreation and respite from the rigors of therapy and recovery, for example, as well as the sense of boredom often felt in the long hours between treatment and therapy sessions. Recreational materials and applications of the present systems may be fully integrated with any and all of the systems and methods described above (and below), and may further be first vetted by hospital staff to be focused on positive, constructive outlets for patients to spend their time and energy, opportunities to build new skills, and creative and enjoyable methods to incorporate specific patient therapies into their leisure time.

In an embodiment, the present system may include an application, or applications, to provide patients access to a considerable digital library of movies, books, and music. Such applications are accessed directly from a home screen of remote content 624 of remote unit 622, for example, by selection of a relevant icon or icons displayed therein. The accessed content may then be played and/or displayed on one or more of the several displays of the system (or other audio/visual components) as desired. Such accessed content may include at least: digital movies; e-books; digital audio books; digital music; and/or specific selections for children. The application(s) may be structured to allow the ability for caregivers to set access on a per-patient and per-ward basis, and also to vet, update, and manage the accessible library content for particular patients or groups of patients.

The Games application of the present system will allow patients and visitors to play an assortment of hospital-approved virtual games, such as board games, adventure games, educational games, etc., including options for children (for children patients, or children visiting a patient using the present systems). In addition to the benefits provided directly to the patient, families and visitors of the patient, through use of the Games application, may occupy their time by the patient's bedside more enjoyably, thereby encouraging more time spent together with a recovering patient.

Similar to the applications discussed above, the Games application may be accessed by a patient (or other user) by selection of the relevant icon from one or more of the several content screens of the present system. Such content may be wall-based games or remote unit based games (where the remote unit is capable of such content display and use). The application may be integrated with existing third party gaming consoles and systems, and may further access the following types of content from a library within the system, or externally loaded in a separate console device (when vetted and approved by hospital staff and caregivers): therapy-related games; family and children's games; sports games; adventure games; strategy games; educational games; "just for fun" games; and custom-built and third party games.

The Skills application of the present system will allow patients to take advantage of long stretches of free time to learn new skills (e.g., job training, musical instruments, complex games such as chess, art, language, etc.) that the patients might not otherwise have time to learn, even after treatment and recovery. Where the patient is a Wounded Warrior still on active duty, a soldier who may be close to recovery, and will rejoin his or her unit, might even be able to focus on learning or enhancing particular technical skills that may be of value before returning to full duty. Certain skill modules may also tie into various therapies for a particular patient, as directed by caregivers.

Similar to the applications discussed above, the Skills application may be accessed by a patient (or other user) by selection of the relevant icon from one or more of the several content screens of the present system. The application may also include, for example, a library of "mini-courses" to choose from in various areas, such as: languages; art and design; music; business; technology; Army; Navy; Air Force; Marines; and Coast Guard. For music modules, musical instruments may be made available to the patient, and specially adapted to particular patient needs or disabilities, if desired. For military-based modules, the Skills application may coordinate with the particular military branches for incorporating specific technical skills, and in keeping with existing U.S. Armed Forces training programs.

The present inventors have further discovered that, for patients undergoing long-term treatment—and particularly Wounded Warriors—finding peace and quiet within a hospital setting is often a significant challenge. Serenity, while important to the healing process, can be ironically elusive in a hectic clinical environment. The present systems and methods thus advantageously alleviate this problem, by integrating within the system specific applications that allow both an array of meditative audio selections, as well as bedside environment control.

For example, the Audio Oasis application of the present system will allow patients to access meditative audio programs that can be controlled at the patient's bedside (through remote unit 622, for example). Hospital environments can be very hectic places, and it can be quite difficult for a patient to find moments of peace and quiet. Moreover, many Wounded Warriors come to a hospital setting with significant vision impairments, as well as other functional disabilities, that will, at least at first, make it very difficult to operate and utilize the present system. Days, weeks, and months with little to do or to occupy the mind can add further suffering and frustration to already-limiting conditions. Through use of the Audio Oasis application, however, much of this stress may be alleviated by accessing (by the patient or a caregiver) programs ranging from nature sounds to meditation, pain mitigation, sleep assistance programs, or simply white noise.

Similar to the applications discussed above, the Audio Oasis application may be accessed by a patient (or other user) by selection of the relevant icon from one or more of the several content screens of the present system. The application may also include one or more of the following selections: meditative looping background audio; therapeutic programs (such as pain mitigation); sleep therapy programs; audio with or without accompanying images or video; customized audio created especially for Wounded Warriors and the present system; and selected programs from third party sources. Sound for the Audio Oasis application may be played on wall screen speakers (e.g., from display 604), and/or pillow speakers (e.g., element 116, FIG. 1) at bedside, or other external or integrated audio components as desired.

An environmental control application of the present system will similarly allow patients to control, from the patient's bedside (through remote unit 622, for example), the brightness, color, and type of light in the room—for example, through lighting system 612, shading system 614, FIG. 6—except when clinical visits are required. Patient rooms (e.g., patient room 102, FIG. 1) may, in addition to windows and standard lighting, include meditative lighting, over which the patient may have control through the environmental control application. The environmental control application may also directly and remotely control motorized blinds, to control the amount of natural light from the window. Through this application, several light sources can be controlled by the patient, and even cooperatively combined with soothing or meditative audio (e.g., Audio Oasis application, above), to transform an ordinary patient room into an "oasis of serenity and tranquility." The application, or its combination with use of other applications, can also effectively create an environment particularly conducive to body work treatments, such as deep-tissue massage. Where desired, the application can also be utilized to access and manipulate other environmental controls, such as heat, air conditioning, humidity, fans, etc., which may be of particular significance when a patient receives care in a home setting.

Similar to the applications discussed above, the environmental control application may be accessed by a patient (or other user) by selection of the relevant icon from one or more of the several content screens of the present system. The application may also include one or more of the following features: bedside control of room brightness and color; bedside control of motorized window blinds; adjustability of temperature, humidity, and related environmental controls; and integral functionality with other audio/visual applications in the present system.

Figure 12:
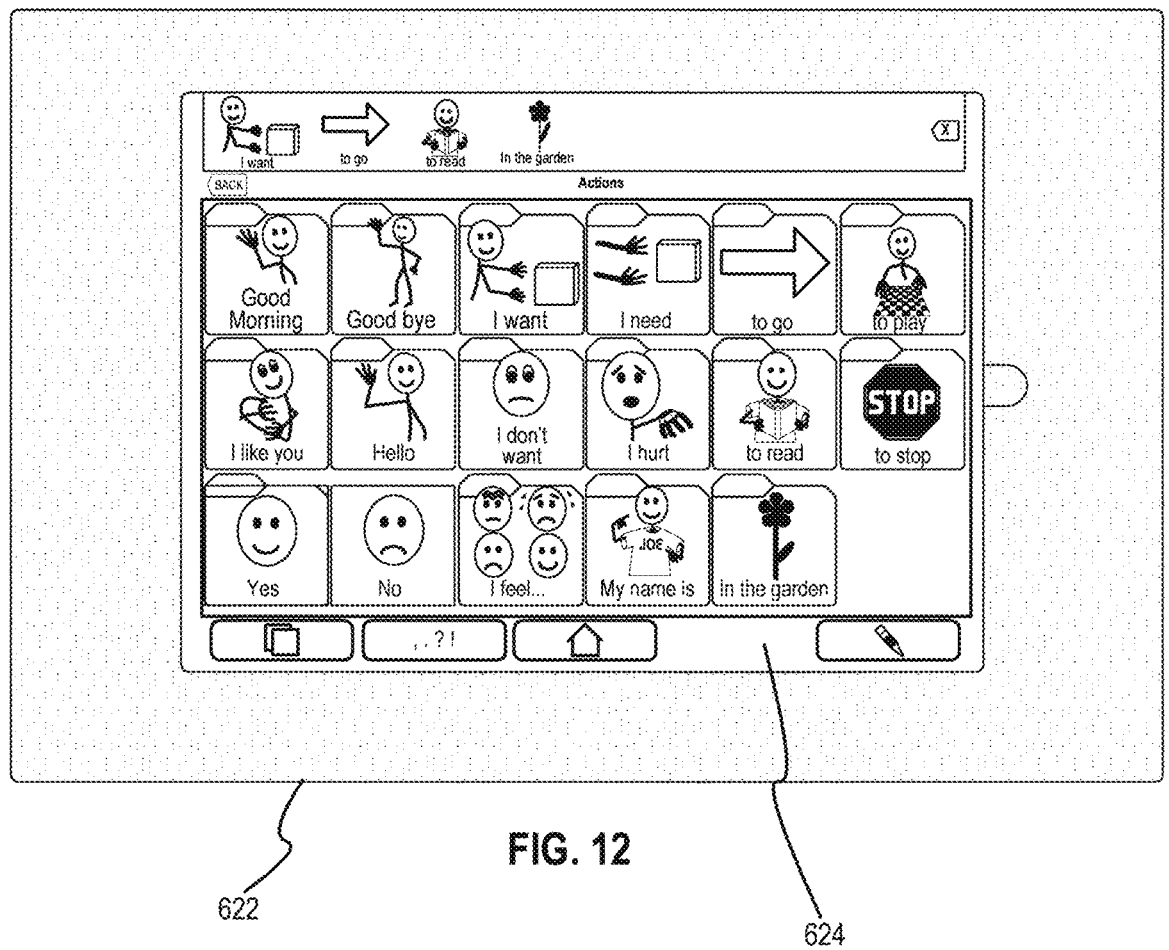
FIG. 12 illustrates a display of a pictorial communication application for assisting speech impaired patients, in an embodiment.

FIG. 12 illustrates a display of a pictorial communication application 1200 for assisting speech-impaired patients, in an embodiment. According to the example illustrated in FIG. 12, communications application 1200, integrated with the present system (systems 100, 500, 600, for example) allows speech-impaired patients to utilize pictorial images and expressions to give "voice" to the patients' needs, thoughts, and feelings by selecting categorized pictures and words which may then also be spoken aloud through one or more of the several audio speakers that may be incorporated within the present system. The application may further allow a patient to even build complex sentences pictorially.

The present system additionally includes applications (and is created for the inclusion and full integration of relevant component devices and necessary software) to accommodate patients with one or more impairments, instead of or in addition to the speech-impairments discussed above. Such other special patient needs may relate to one or more of the following abilities: vision; hearing; dexterity; and mobility.

In an embodiment, for visually impaired patients, remote unit 622 can be activated to access a "voice-over" application, which may give the patient audio cues for navigating remote content 624 of system 600 (e.g., "double-tap to open"). Once such audio cues are understood and familiar to a patient, navigation becomes even easier thereby. Other features and applications available for visually impaired users include: screen magnification tools; text enlargement (apart from the entire screen); and text reversal to white text on a black background, for intensified contrast and readability.

In an embodiment, for hearing impaired patients, remote unit 622 can be activated to access closed captioning for supported videos, as well as enhanced volume controls and equalizers for other audio capabilities and features of system 600.

In an embodiment, for patients that may not have full use (or any use) of arms, hands, and/or fingers, a special stylus (not shown) may be provided for use with remote unit 622 and remote content 624. The stylus can be held like a pen, where the patient has such capability, or attached to a prosthetic device, as appropriate for the particular patient. Patients who have difficulty or inability typing can use the stylus to open a dictation application available on system 600, to convert voiced dictation into digital text, which digital text may then be copied, pasted, and/or saved into applications throughout the system that utilize text.

Figure 14:
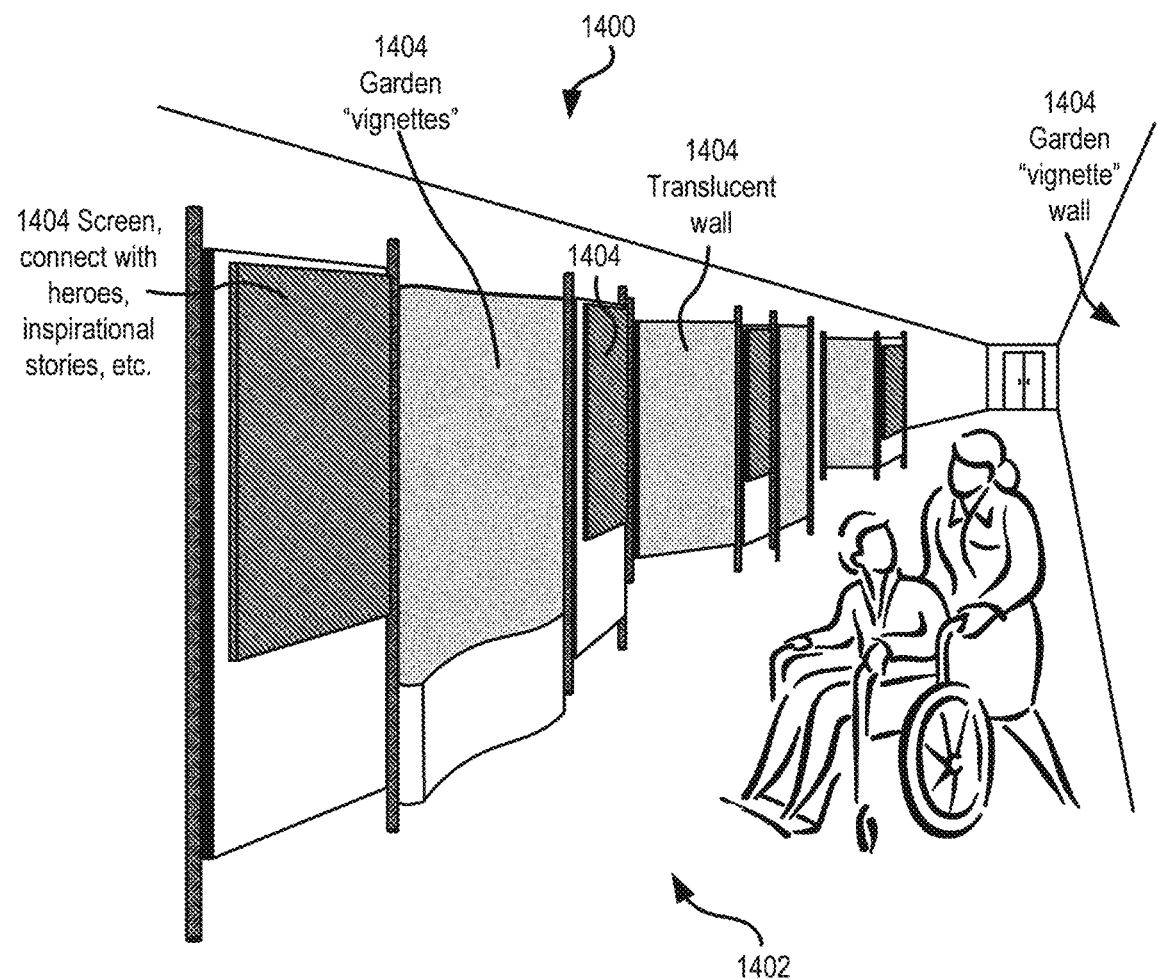
FIG. 14 illustrates an example of a corridor integrated as a component of the present system, in an embodiment.

FIG. 14 illustrates an example of a corridor integrated as a component of the present system, in an embodiment. According to the example illustrated in FIG. 14, the present systems and methods may be further integrated to "follow" the patient, if desired, as the patient increases his or her mobility outside of the patient room and/or travels throughout a larger hospital facility and environment. In the example shown, system 1400 includes a hallway or access corridor 1402 and one or more corridor displays 1404. Access corridor 1402 may serve to lead a patient from his or her room, along a path that may itself provide informational and uplifting content 1406, to physical healing gardens (not shown) at another location in the hospital facility. Access corridor 1402 may further serve as an introduction to the gardens—physical or virtual—as well as an incentive for motivating a patient to work toward visiting the physical garden in person, when possible for the patient. According to system 1400, which may include and/or integrate any and all of the systems and methods described above, an unbroken continuum of healing, communication, and inspiration may be formed throughout a hospital facility for patients to reconnect to nature and the outside world.

Some patients may be capable of visiting a physical healing gardens very soon into their hospitalization, while other patients may experience a slower recovery process, requiring progressive steps before eventually reaching the physical healing gardens. Through utilization of access corridors 1402 (which may also be elevators, lobbies, and/or entrances of a hospital facility) the virtual gardens of patient rooms, described above, may be gradually linked to the physical gardens elsewhere in the facility to promote holistic healing, as garden concepts become more apparent to the patient. Such gradual movement from a hospital setting to a natural setting may also advantageously instill an enhanced feeling of serenity to the patient. Content 1406 on the corridor displays 1404 may include interpretative information, explanatory graphics, important information, and interactive applications, similar to the systems and methods described above.

In an embodiment, garden "vignettes" may also be placed at various strategic intervals, that is, as content 1406 on corridor displays 1404, to create a "bread crumb trail" that leads to the exterior healing gardens. The "trail" may be synchronized with a signal from a remote unit (e.g., remote unit 622) carried by, or attached to a unit holder (not shown) of a wheelchair or wheeled bed (patient transport) used by, the patient as the patient moves throughout the hospital facility. These virtual "natural" elements throughout the facility may help transform an otherwise impersonal and relatively sterile environment into one that provides additional healing opportunities for the patient and the patient's visitors and caregivers. For particularly large facilities, corridor content may also provide directions to a patient to or from the patient's room, or other areas of the facility. Remote unit 622 could also include one or more applications to access corridor displays 1404, or portions thereof, to locally function as navigation/content panes (similar to elements 606/608, above) when the patient is away from the patient room.

In an embodiment, the present systems and methods may also include, in addition to the virtual and physical gardens described above, one or more transition spaces to accommodate indoor gardening activities on a smaller scale. Patients and visitors may be able to spend time, alone or with others, year-round in comfortable, climate-controlled spaces that may be mitigated from the elements, yet still surrounded by vegetation and greenery. In such transition spaces, patients may additionally be introduced (in person or virtually) to role models and mentors who traveled a similar path and triumphed in their own journeys. An additional or alternative transition space (not shown) could be provided by an atrium that leads to the physical (and often outdoor) healing gardens. Such spaces may provide patients who are ready for public interaction to spend time in daylight and fresh air, yet still remain somewhat protected from harsher natural elements for which the patient may not yet be ready.

In an embodiment, the atrium may be a first-time, visitor-friendly space, that is easily navigated and understood by those unfamiliar with it. The atrium may additionally feature a tribute wall, dedicated specifically to Wounded Warriors, and encourage patients, family members, friends, visitors and staff to leave general messages to such men and women who serve, thanking them for their dedication and sacrifice, expressing personal thoughts of appreciation, and communicating words of encouragement or positive quotations. Messages may be placed in the "cracks" between stones on the tribute wall, either virtually in digital text (at the wall or through a remote unit), or physically in the material between display panes, according to the specific design and capability of the tribute wall.

The atrium may also offer opportunities for intimate family gatherings, small group conversations, and semi-private times of reflection and contemplation for recovering patients. Where an actual water feature is not possible, or alternatively, in addition to such an actual water feature, the atrium may further include a virtual water feature within the space that "meanders," then disappears, and later may be rediscovered "springing" forward toward the exterior healing gardens, similar to the "breadcrumb trail," described above. The innermost spaces within the atrium may further focus on more private activities for recovering patients, such as relaxing or intimately socializing with family members and friends.

In an embodiment, display 1404 may be interactive tabletops, which, in addition to the features and abilities described above, may additionally function as virtual chess- or checkers-boards, or even a "virtual scrapbook" for patient photographs and papers (which may be stored on remote unit 622, for example, and then removed from view on display 1404 when desired or when remote unit 622 is moved away from the vicinity of display 1404).

In an embodiment, display 1404 may be a "welcoming wall" at an entrance to a hospital facility that may orient patients, family, friends, and visitors to the purpose, history, and functions of the present systems and methods, in addition to the facility itself. The welcoming wall may further introduce viewers to specific activities and features of the facility and the healing gardens (e.g., group gatherings, planned or informal activities, specific patient/soldier recognitions or dedications/achievements, barbeques, star gazing, treasure hunts, etc.), as well as offer explanations and information to be discovered within the facility and garden(s).

Changes may be made in the above methods and systems without departing from the scope hereof. It should thus be noted that the matter contained in the above description or shown in the accompanying drawings should be interpreted as illustrative, and not in a limiting sense. The following claims are intended to cover generic and specific features described herein, as well as a scope of the present systems and methods, which, as a matter of language, might be said to fall therebetween.

The invention claimed is:

1. A method of configuring a personal living environment of a long-term patient to promote enhanced healing of said patient, comprising:
   providing a central computer controllable via a remote unit;
   coupling said central computer to a plurality of output devices and at least one sensor; said plurality of output devices including displays and speakers; at least one of said displays comprising a navigation pane and a content pane; said content pane configured to display content selected using any one of said remote unit and said navigation pane;
   arranging said plurality of output devices in said personal living environment;

presenting on said navigation pane patient selectable objective parameters and subjective parameters relating to said patient;

obtaining an input from said patient, and in response to said input, representing on said content pane a relationship, characterized over a time period, between said subjective parameters and said objective parameters selected by said patient;

shifting presentation of content from one of said plurality of output devices to another of said plurality of output devices based on a proximity of said patient detected by said at least one sensor.

2. The method of claim 1, further comprising providing meditative lighting in said personal living environment.

3. The method of claim 2, wherein said remote unit is usable to control said meditative lighting.

4. The method of claim 1, wherein said content comprises healing content, said healing content including a garden element.

5. The method of claim 1, wherein said input includes a numeric value and a comment from said patient.

6. The method of claim 1, wherein the remote unit is a smart phone.

7. The method of claim 1, wherein the remote unit is a tablet.

8. The method of claim 1, further comprising docking said remote unit to a docking station coupled to a bed of said patient.

9. The method of claim 1, wherein at least one of said displays has a first mode and a second mode, said first mode being configured for the passage of light through said display, said second mode being configured for the presentation of content on said display.

10. The method of claim 1, wherein:
said patient is bed-bound; and
said displays are arranged such that they surround said bed-bound patient.

11. The method of claim 1, wherein said at least one sensor includes a video camera.

12. The method of claim 1, wherein said personal living environment is within a home of said patient.

13. The method of claim 1, further comprising creating a log of a healing progress of said patient, said log comprising images selected by said patient to indicate a mood of said patient at a given time.

14. A method of configuring a personal living environment of a long-term patient to promote enhanced healing of said patient, comprising:

providing a central computer controllable via a remote unit;

coupling said central computer to a plurality of output devices and at least one sensor; said plurality of output devices including displays and speakers;

arranging said plurality of output devices in said personal living environment;

presenting on at least one of said displays patient selectable objective parameters and subjective parameters relating to said patient;

obtaining an input from said patient, and in response to said input, representing on at least one of said displays a relationship, characterized over a time period, between said subjective parameters and said objective parameters selected by said patient;

shifting presentation of content from one of said plurality of output devices to another of said plurality of output devices based on a proximity of said patient detected by said at least one sensor.

15. The method of claim 14, further comprising situating at least some of said plurality of output devices in an assembly, said assembly including a desk unit.

16. The method of claim 14, wherein said remote unit is usable to control a window shade.

17. The method of claim 14, wherein at least one of said displays is configured to selectively pass light therethrough and to display content thereon.

18. The method of claim 14, further comprising creating a log of a healing progress of said patient, said log comprising images selected by said patient to indicate a mood of said patient.

19. A method of configuring a personal living environment of a patient, comprising:

providing a central computer controllable via a remote unit;

coupling said central computer to a plurality of output devices and at least one sensor; said plurality of output devices including displays and speakers;

presenting on at least one of said displays objective parameters and subjective parameters;

obtaining an input from said patient, and in response to said input, representing on at least one of said displays a relationship, characterized over a time period, between said subjective parameters and said objective parameters;

shifting presentation of content from one of said plurality of output devices to another of said plurality of output devices based on a proximity of said patient detected by said at least one sensor.

20. The method of claim 19, wherein said personal healing environment includes a room and a corridor, each having at least some of said plurality of output devices configured therein.

* * * * *